US012655413B2

(12) United States Patent
Kim et al.

(10) Patent No.: US 12,655,413 B2
(45) Date of Patent: Jun. 16, 2026

(54) FRAGMENTED GRS POLYPEPTIDE AND VARIANT THEREOF, AND USE THEREOF

(71) Applicant: CUREBIO THERAPEUTICS, Suwon-si (KR)

(72) Inventors: Sunghoon Kim, Suwon-si (KR); Peter Charles Goughnour, Suwon-si (KR)

(73) Assignee: NIBEC CO., LTD., Seoul (KR)

( * ) Notice: Subject to any disclaimer, the term of this patent is extended or adjusted under 35 U.S.C. 154(b) by 1205 days.

(21) Appl. No.: 17/057,363

(22) PCT Filed: May 15, 2019

(86) PCT No.: PCT/KR2019/005849
§ 371 (c)(1),
(2) Date: Nov. 20, 2020

(87) PCT Pub. No.: WO2019/225899
PCT Pub. Date: Nov. 28, 2019

(65) Prior Publication Data
US 2021/0198650 A1 Jul. 1, 2021

(30) Foreign Application Priority Data
May 23, 2018 (KR) ........................ 10-2018-0058647

(51) Int. Cl.
*C12N 9/00* (2006.01)
*A61K 38/00* (2006.01)
(Continued)

(52) U.S. Cl.
CPC ................ *C12N 9/93* (2013.01); *A61K 45/06* (2013.01); *A61K 47/60* (2017.08); *A61P 35/00* (2018.01);
(Continued)

(58) Field of Classification Search
CPC combination set(s) only.
See application file for complete search history.

(56) References Cited

U.S. PATENT DOCUMENTS

| 8,404,471 B2 * | 3/2013 | Greene .................... C07K 1/14 435/71.1 |
| 9,274,113 B2 * | 3/2016 | Kim ..................... G01N 33/573 |

(Continued)

FOREIGN PATENT DOCUMENTS

| JP | 2014530019 A | 11/2014 |
| KR | 10-2010-0040697 A | 4/2010 |

(Continued)

OTHER PUBLICATIONS

Garewal HS, Ramsey L, Kaugars G, Boyle J. Clinical experience with the micronucleus assay. J Cell Biochem Suppl. 1993;17F:206-12. doi: 10.1002/jcb.240531031. PMID: 8412196. (Year: 1993).*

(Continued)

*Primary Examiner* — Jeffrey Stucker
*Assistant Examiner* — Laura A Essex
(74) *Attorney, Agent, or Firm* — James S. Keddie; Bozicevic, Field & Francis LLP

(57) ABSTRACT
The present invention relates to a fragmented GRS polypeptide and a variant thereof, and a use thereof and, more specifically, to: an isolated polypeptide consisting of 8 to 170 consecutive amino acids including amino acids 531 to 538 in the amino acid sequence represented by SEQ ID NO: 1 or a polypeptide consisting of a variant having a sequence homology of 80% or more with the polypeptide; a fusion protein and a complex comprising the polypeptide; a polynucleotide coding for the polypeptide; and a use thereof for the prevention and treatment of neoplastic diseases, the detection of cancer cells, imaging, and drug delivery.

25 Claims, 17 Drawing Sheets

Specification includes a Sequence Listing.

(51) Int. Cl.

| | |
|---|---|
| *A61K 45/06* | (2006.01) |
| *A61K 47/60* | (2017.01) |
| *A61P 35/00* | (2006.01) |
| *G01N 33/50* | (2006.01) |
| *G01N 33/574* | (2006.01) |
| *G01N 33/575* | (2026.01) |

(52) U.S. Cl.

CPC ....... *G01N 33/5011* (2013.01); *G01N 33/575* (2026.01); *A61K 38/00* (2013.01); *C12Y 601/01014* (2013.01); *G01N 2333/9015* (2013.01)

(56) References Cited

U.S. PATENT DOCUMENTS

| | | |
|---|---|---|
| 2008/0148432 A1 | 6/2008 | Abad |
| 2010/0028352 A1 | 2/2010 | Greene et al. |
| 2011/0256119 A1 | 10/2011 | Kim et al. |

FOREIGN PATENT DOCUMENTS

| | | | | |
|---|---|---|---|---|
| KR | 10-2013-0038768 A | 4/2013 | | |
| KR | 20180045336 A | 5/2018 | | |
| WO | WO 2012/158945 A2 | 11/2012 | | |
| WO | WO-2013055101 A1 * | 4/2013 | ........... | G01N 33/573 |
| WO | WO 2017/184590 A1 | 10/2017 | | |

OTHER PUBLICATIONS

Lichtman MA. A Bacterial Cause of Cancer: An Historical Essay. Oncologist. May 2017;22(5):542-548. doi: 10.1634/theoncologist. 2017-0007. Epub Apr. 21, 2017. PMID: 28432224; PMCID: PMC5423514. (Year: 2017).*

Rashid HU, Xu Y, Muhammad Y, Wang L, Jiang J. Research advances on anticancer activities of matrine and its derivatives: An updated overview. Eur J Med Chem. Jan. 1, 2019;161:205-238. doi: 10.1016/j.ejmech.2018.10.037. Epub Oct. 19, 2018. PMID: 30359819. (Year: 2019).*

Wan Y, Li Y, Yan C, Yan M, Tang Z. Indole: A privileged scaffold for the design of anti-cancer agents. Eur J Med Chem. Dec. 1, 2019;183:111691. doi: 10.1016/j.ejmech.2019.111691. Epub Sep. 11, 2019. PMID: 31536895. (Year: 2019).*

Naatsaari L, Krainer FW, Schubert M, Glieder A, Thallinger GG. Peroxidase gene discovery from the horseradish transcriptome. BMC Genomics. Mar. 24, 2014;15:227. doi: 10.1186/1471-2164-15-227. PMID: 24666710; PMCID: PMC3987668. (Year: 2014).*

Han et al., "Secreted human glycyl-tRNA synthetase as a natural immune surveillance agent against tumorigenesis", Medicinal Bioconvergence Research Center, and Department of Molecular Medicine and Biopharmaceutical Sciences, Graduate School of Convergence Technology, Seoul National University, 2014.

NCBI. GenBank accession No. AAH07722.1, 2006.

Park, et al., "Secreted human glycyl-tRNA synthetase implicated in defense against ERK-activated tumorigenesis", PNAS, 2012, 109(11): E640-E647.

* cited by examiner

GRS full length
(1-685)

GRS-F4
(511-685)

GRS-F4-NT-1
(526-685)

GRS-F4-NT-2
(538-685)

GRS-F4-NT-3
(558-685)

GRS-DP
(531-600aa, 70mer, 7.977kD)

MYTVFERTFH VREGDEQRTF FSFPAVVAPF KCSVLPLSQN QEFRPFVKEL SEALTRHGVS HKVDDSSGSI

GRS-DP-A linear
(531-555aa, 25mer, 3.079kD)

MYTVFERTFHVREGDEQRTFFSFPA

Mono-sulfide Link

GRS-DP-A cyclic
(531-555aa, 25mer, 3.083kD)

CYTVFERTFHVREGDEQRTFFSFPC

GRS-DP-B
(531-538aa, 8mer,
1.027kD)

MYTVFERT

GRS-DP-C
(538-552aa, 15mer,
1.855kD)

TFHVREGDEQRTFFS

| Protein | Tm (°C) |
|---------|---------|
| GRS | 55.05 |
| GRS-DP | 53.44 |

GRS

GRS-DP-A
cyclic

GRS-DP-A
linear

GRS-DP-B

Around 5-7 days, the tumor will
be around 100m³ then inject
GRS/Peptide injection >600m³ or significant difference
compared to control then
harvest mice 0    5    7    9    11    13    15    17    19    21    Days Cell line SC injection
(1X10⁷cells)

SEQUENCE LISTING

```
<160> NUMBER OF SEQ ID NOS: 46

<210> SEQ ID NO 1
<211> LENGTH: 685
<212> TYPE: PRT
<213> ORGANISM: Artificial Sequence
<220> FEATURE:
<223> OTHER INFORMATION: human GRS full length

<400> SEQUENCE: 1

Met Asp Gly Ala Gly Ala Glu Glu Val Leu Ala Pro Leu Arg Leu Ala
1               5                   10                  15

Val Arg Gln Gln Gly Asp Leu Val Arg Lys Leu Lys Glu Asp Lys Ala
                20                  25                  30

Pro Gln Val Asp Val Asp Lys Ala Val Ala Glu Leu Lys Ala Arg Lys
            35                  40                  45

Arg Val Leu Glu Ala Lys Glu Leu Ala Leu Gln Pro Lys Asp Asp Ile
        50                  55                  60

Val Asp Arg Ala Lys Met Glu Asp Thr Leu Lys Arg Arg Phe Phe Tyr
65                  70                  75                  80

Asp Gln Ala Phe Ala Ile Tyr Gly Gly Val Ser Gly Leu Tyr Asp Phe
                85                  90                  95

Gly Pro Val Gly Cys Ala Leu Lys Asn Asn Ile Ile Gln Thr Trp Arg
            100                 105                 110

Gln His Phe Ile Gln Glu Glu Gln Ile Leu Glu Ile Asp Cys Thr Met
        115                 120                 125

Leu Thr Pro Glu Pro Val Leu Lys Thr Ser Gly His Val Asp Lys Phe
        130                 135                 140

Ala Asp Phe Met Val Lys Asp Val Lys Asn Gly Glu Cys Phe Arg Ala
145                 150                 155                 160

Asp His Leu Leu Lys Ala His Leu Gln Lys Leu Met Ser Asp Lys Lys
                165                 170                 175

Cys Ser Val Glu Lys Lys Ser Glu Met Glu Ser Val Leu Ala Gln Leu
            180                 185                 190
```

-continued

```
Asp Asn Tyr Gly Gln Gln Glu Leu Ala Asp Leu Phe Val Asn Tyr Asn
    195                 200             205

Val Lys Ser Pro Ile Thr Gly Asn Asp Leu Ser Pro Pro Val Ser Phe
    210                 215             220

Asn Leu Met Phe Lys Thr Phe Ile Gly Pro Gly Gly Asn Met Pro Gly
225                 230             235             240

Tyr Leu Arg Pro Glu Thr Ala Gln Gly Ile Phe Leu Asn Phe Lys Arg
                245             250             255

Leu Leu Glu Phe Asn Gln Gly Lys Leu Pro Phe Ala Ala Ala Gln Ile
                260             265             270

Gly Asn Ser Phe Arg Asn Glu Ile Ser Pro Arg Ser Gly Leu Ile Arg
    275                 280             285

Val Arg Glu Phe Thr Met Ala Glu Ile Glu His Phe Val Asp Pro Ser
    290                 295             300

Glu Lys Asp His Pro Lys Phe Gln Asn Val Ala Asp Leu His Leu Tyr
305                 310             315             320

Leu Tyr Ser Ala Lys Ala Gln Val Ser Gly Gln Ser Ala Arg Lys Met
                325             330             335

Arg Leu Gly Asp Ala Val Glu Gln Gly Val Ile Asn Asn Thr Val Leu
                340             345             350

Gly Tyr Phe Ile Gly Arg Ile Tyr Leu Tyr Leu Thr Lys Val Gly Ile
                355             360             365

Ser Pro Asp Lys Leu Arg Phe Arg Gln His Met Glu Asn Glu Met Ala
    370                 375             380

His Tyr Ala Cys Asp Cys Trp Asp Ala Glu Ser Lys Thr Ser Tyr Gly
385                 390             395             400

Trp Ile Glu Ile Val Gly Cys Ala Asp Arg Ser Cys Tyr Asp Leu Ser
                405             410             415

Cys His Ala Arg Ala Thr Lys Val Pro Leu Val Ala Glu Lys Pro Leu
                420             425             430

Lys Glu Pro Lys Thr Val Asn Val Val Gln Phe Glu Pro Ser Lys Gly
    435                 440             445

Ala Ile Gly Lys Ala Tyr Lys Lys Asp Ala Lys Leu Val Met Glu Tyr
    450                 455             460

Leu Ala Ile Cys Asp Glu Cys Tyr Ile Thr Glu Ile Glu Met Leu Leu
465                 470             475             480

Asn Glu Lys Gly Glu Phe Thr Ile Glu Thr Glu Gly Lys Thr Phe Gln
                485             490             495

Leu Thr Lys Asp Met Ile Asn Val Lys Arg Phe Gln Lys Thr Leu Tyr
                500             505             510

Val Glu Glu Val Val Pro Asn Val Ile Glu Pro Ser Phe Gly Leu Gly
    515                 520             525

Arg Ile Met Tyr Thr Val Phe Glu His Thr Phe His Val Arg Glu Gly
    530                 535             540

Asp Glu Gln Arg Thr Phe Phe Ser Phe Pro Ala Val Val Ala Pro Phe
545                 550             555             560

Lys Cys Ser Val Leu Pro Leu Ser Gln Asn Gln Glu Phe Met Pro Phe
                565             570             575

Val Lys Glu Leu Ser Glu Ala Leu Thr Arg His Gly Val Ser His Lys
                580             585             590

Val Asp Asp Ser Ser Gly Ser Ile Gly Arg Arg Tyr Ala Arg Thr Asp
    595                 600             605
```

-continued

```
Glu Ile Gly Val Ala Phe Gly Val Thr Ile Asp Phe Asp Thr Val Asn
    610             615             620

Lys Thr Pro His Thr Ala Thr Leu Arg Asp Arg Asp Ser Met Arg Gln
625             630             635             640

Ile Arg Ala Glu Ile Ser Glu Leu Pro Ser Ile Val Gln Asp Leu Ala
            645             650             655

Asn Gly Asn Ile Thr Trp Ala Asp Val Glu Ala Arg Tyr Pro Leu Phe
            660             665             670

Glu Gly Gln Glu Thr Gly Lys Lys Glu Thr Ile Glu Glu
        675             680             685

<210> SEQ ID NO 2
<211> LENGTH: 8
<212> TYPE: PRT
<213> ORGANISM: Artificial Sequence
<220> FEATURE:
<223> OTHER INFORMATION: GRS-DP-B(GRS 531-538)

<400> SEQUENCE: 2

Met Tyr Thr Val Phe Glu His Thr
1               5

<210> SEQ ID NO 3
<211> LENGTH: 25
<212> TYPE: PRT
<213> ORGANISM: Artificial Sequence
<220> FEATURE:
<223> OTHER INFORMATION: GRS-DP-A linear (GRS 531-555, linear)

<400> SEQUENCE: 3

Met Tyr Thr Val Phe Glu His Thr Phe His Val Arg Glu Gly Asp Glu
1               5               10              15

Gln Arg Thr Phe Phe Ser Phe Pro Ala
            20              25

<210> SEQ ID NO 4
<211> LENGTH: 70
<212> TYPE: PRT
<213> ORGANISM: Artificial Sequence
<220> FEATURE:
<223> OTHER INFORMATION: GRS-DP (GRS 531-600)

<400> SEQUENCE: 4

Met Tyr Thr Val Phe Glu His Thr Phe His Val Arg Glu Gly Asp Glu
1               5               10              15

Gln Arg Thr Phe Phe Ser Phe Pro Ala Val Val Ala Pro Phe Lys Cys
            20              25              30

Ser Val Leu Pro Leu Ser Gln Asn Gln Glu Phe Met Pro Phe Val Lys
        35              40              45

Glu Leu Ser Glu Ala Leu Thr Arg His Gly Val Ser His Lys Val Asp
    50              55              60

Asp Ser Ser Gly Ser Ile
65              70

<210> SEQ ID NO 5
<211> LENGTH: 155
<212> TYPE: PRT
<213> ORGANISM: Artificial Sequence
<220> FEATURE:
<223> OTHER INFORMATION: GRS 531-685

<400> SEQUENCE: 5
```

```
Met Tyr Thr Val Phe Glu His Thr Phe His Val Arg Glu Gly Asp Glu
1               5               10              15

Gln Arg Thr Phe Phe Ser Phe Pro Ala Val Val Ala Pro Phe Lys Cys
        20              25              30

Ser Val Leu Pro Leu Ser Gln Asn Gln Glu Phe Met Pro Phe Val Lys
        35              40              45

Glu Leu Ser Glu Ala Leu Thr Arg His Gly Val Ser His Lys Val Asp
    50              55              60

Asp Ser Ser Gly Ser Ile Gly Arg Arg Tyr Ala Arg Thr Asp Glu Ile
65              70              75              80

Gly Val Ala Phe Gly Val Thr Ile Asp Phe Asp Thr Val Asn Lys Thr
            85              90              95

Pro His Thr Ala Thr Leu Arg Asp Arg Asp Ser Met Arg Gln Ile Arg
            100             105             110

Ala Glu Ile Ser Glu Leu Pro Ser Ile Val Gln Asp Leu Ala Asn Gly
        115             120             125

Asn Ile Thr Trp Ala Asp Val Glu Ala Arg Tyr Pro Leu Phe Glu Gly
    130             135             140

Gln Glu Thr Gly Lys Lys Glu Thr Ile Glu Glu
145             150             155
```

```
<210> SEQ ID NO 6
<211> LENGTH: 160
<212> TYPE: PRT
<213> ORGANISM: Artificial Sequence
<220> FEATURE:
<223> OTHER INFORMATION: GRS-F4-NT-1(GRS 526-685)

<400> SEQUENCE: 6
```

```
Gly Leu Gly Arg Ile Met Tyr Thr Val Phe Glu His Thr Phe His Val
1               5               10              15

Arg Glu Gly Asp Glu Gln Arg Thr Phe Phe Ser Phe Pro Ala Val Val
            20              25              30

Ala Pro Phe Lys Cys Ser Val Leu Pro Leu Ser Gln Asn Gln Glu Phe
        35              40              45

Met Pro Phe Val Lys Glu Leu Ser Glu Ala Leu Thr Arg His Gly Val
    50              55              60

Ser His Lys Val Asp Asp Ser Ser Gly Ser Ile Gly Arg Arg Tyr Ala
65              70              75              80

Arg Thr Asp Glu Ile Gly Val Ala Phe Gly Val Thr Ile Asp Phe Asp
            85              90              95

Thr Val Asn Lys Thr Pro His Thr Ala Thr Leu Arg Asp Arg Asp Ser
            100             105             110

Met Arg Gln Ile Arg Ala Glu Ile Ser Glu Leu Pro Ser Ile Val Gln
        115             120             125

Asp Leu Ala Asn Gly Asn Ile Thr Trp Ala Asp Val Glu Ala Arg Tyr
    130             135             140

Pro Leu Phe Glu Gly Gln Glu Thr Gly Lys Lys Glu Thr Ile Glu Glu
145             150             155             160
```

```
<210> SEQ ID NO 7
<211> LENGTH: 25
<212> TYPE: PRT
<213> ORGANISM: Artificial Sequence
<220> FEATURE:
<223> OTHER INFORMATION: GRS-DP-A  cyclic (GRS-DP-A variant cyclic)

<400> SEQUENCE: 7
```

Cys Tyr Thr Val Phe Glu His Thr Phe His Val Arg Glu Gly Asp Glu
1               5                   10                  15

Gln Arg Thr Phe Phe Ser Phe Pro Cys
            20                  25

<210> SEQ ID NO 8
<211> LENGTH: 24
<212> TYPE: DNA
<213> ORGANISM: Artificial Sequence
<220> FEATURE:
<223> OTHER INFORMATION: neucleotide sequence of GRS-DP-B(GRS 531-538)

<400> SEQUENCE: 8
atgtatacgg tatttgaaca taca                                          24

<210> SEQ ID NO 9
<211> LENGTH: 75
<212> TYPE: DNA
<213> ORGANISM: Artificial Sequence
<220> FEATURE:
<223> OTHER INFORMATION: neucleotide sequence of GRS-DP-A linear (GRS
      531-555, linear)

<400> SEQUENCE: 9
atgtatacgg tatttgaaca tacattccat gtacgagaag gagatgaaca gagaacattc     60
ttcagtttcc ctgct                                                    75

<210> SEQ ID NO 10
<211> LENGTH: 210
<212> TYPE: DNA
<213> ORGANISM: Artificial Sequence
<220> FEATURE:
<223> OTHER INFORMATION: neucleotide sequence of GRS-DP (GRS 531-600)

<400> SEQUENCE: 10
atgtatacgg tatttgaaca tacattccat gtacgagaag gagatgaaca gagaacattc     60
ttcagtttcc ctgctgtagt tgctccattc aaatgttccg tcctcccact gagccaaaac    120
caggagttca tgccatttgt caaggaatta tcggaagccc tgaccaggca tggagtatct    180
cacaaagtag acgattcctc tgggtcaatc                                    210

<210> SEQ ID NO 11
<211> LENGTH: 75
<212> TYPE: DNA
<213> ORGANISM: Artificial Sequence
<220> FEATURE:
<223> OTHER INFORMATION: neucleotide sequence of GRS-DP-A  cyclic (GRS-
      DP-A variant cyclic)

<400> SEQUENCE: 11
tgttatacgg tatttgaaca tacattccat gtacgagaag gagatgaaca gagaacattc     60
ttcagtttcc cttgt                                                    75

<210> SEQ ID NO 12
<211> LENGTH: 15
<212> TYPE: PRT
<213> ORGANISM: Artificial Sequence
<220> FEATURE:
<223> OTHER INFORMATION: GRS-DP-C (GRS 538-552)

<400> SEQUENCE: 12

Thr Phe His Val Arg Glu Gly Asp Glu Gln Arg Thr Phe Phe Ser
1               5                   10                  15

<210> SEQ ID NO 13
<211> LENGTH: 45
<212> TYPE: DNA
<213> ORGANISM: Artificial Sequence
<220> FEATURE:
<223> OTHER INFORMATION: neucleotide sequence of GRS-DP-C (GRS 538-552)

<400> SEQUENCE: 13
acattccatg tacgagaagg agatgaacag agaacattct tcagt                    45

<210> SEQ ID NO 14
<211> LENGTH: 175
<212> TYPE: PRT
<213> ORGANISM: Artificial Sequence
<220> FEATURE:
<223> OTHER INFORMATION: GRS-F4

<400> SEQUENCE: 14

Leu Tyr Val Glu Glu Val Val Pro Asn Val Ile Glu Pro Ser Phe Gly
1               5                   10                  15

Leu Gly Arg Ile Met Tyr Thr Val Phe Glu His Thr Phe His Val Arg
            20                  25                  30

Glu Gly Asp Glu Gln Arg Thr Phe Phe Ser Phe Pro Ala Val Val Ala
        35                  40                  45

Pro Phe Lys Cys Ser Val Leu Pro Leu Ser Gln Asn Gln Glu Phe Met
    50                  55                  60

Pro Phe Val Lys Glu Leu Ser Glu Ala Leu Thr Arg His Gly Val Ser
65                  70                  75                  80

His Lys Val Asp Asp Ser Ser Gly Ser Ile Gly Arg Arg Tyr Ala Arg
                85                  90                  95

Thr Asp Glu Ile Gly Val Ala Phe Gly Val Thr Ile Asp Phe Asp Thr
            100                 105                 110

Val Asn Lys Thr Pro His Thr Ala Thr Leu Arg Asp Arg Asp Ser Met
        115                 120                 125

Arg Gln Ile Arg Ala Glu Ile Ser Glu Leu Pro Ser Ile Val Gln Asp
    130                 135                 140

Leu Ala Asn Gly Asn Ile Thr Trp Ala Asp Val Glu Ala Arg Tyr Pro
145                 150                 155                 160

Leu Phe Glu Gly Gln Glu Thr Gly Lys Lys Glu Thr Ile Glu Glu
            165                 170                 175

<210> SEQ ID NO 15
<211> LENGTH: 10
<212> TYPE: PRT
<213> ORGANISM: Artificial Sequence
<220> FEATURE:
<223> OTHER INFORMATION: GRS-EX-1

<400> SEQUENCE: 15

Met Tyr Thr Val Phe Glu His Thr Phe His
1               5                   10

<210> SEQ ID NO 16
<211> LENGTH: 10
<212> TYPE: PRT
<213> ORGANISM: Artificial Sequence
<220> FEATURE:
<223> OTHER INFORMATION: GRS-EX-2

<400> SEQUENCE: 16

```
Ile Met Tyr Thr Val Phe Glu His Thr Phe
1               5                   10

<210> SEQ ID NO 17
<211> LENGTH: 10
<212> TYPE: PRT
<213> ORGANISM: Artificial Sequence
<220> FEATURE:
<223> OTHER INFORMATION: GRS-EX-3

<400> SEQUENCE: 17

Arg Ile Met Tyr Thr Val Phe Glu His Thr
1               5                   10

<210> SEQ ID NO 18
<211> LENGTH: 13
<212> TYPE: PRT
<213> ORGANISM: Artificial Sequence
<220> FEATURE:
<223> OTHER INFORMATION: GRS-EX-4

<400> SEQUENCE: 18

Arg Ile Met Tyr Thr Val Phe Glu His Thr Phe His Val
1               5                   10

<210> SEQ ID NO 19
<211> LENGTH: 15
<212> TYPE: PRT
<213> ORGANISM: Artificial Sequence
<220> FEATURE:
<223> OTHER INFORMATION: GRS-EX-5

<400> SEQUENCE: 19

Met Tyr Thr Val Phe Glu His Thr Phe His Val Arg Glu Gly Asp
1               5                   10                  15

<210> SEQ ID NO 20
<211> LENGTH: 20
<212> TYPE: PRT
<213> ORGANISM: Artificial Sequence
<220> FEATURE:
<223> OTHER INFORMATION: GRS-EX-6

<400> SEQUENCE: 20

Gly Leu Gly Arg Ile Met Tyr Thr Val Phe Glu His Thr Phe His Val
1               5                   10                  15

Arg Glu Gly Asp
            20

<210> SEQ ID NO 21
<211> LENGTH: 15
<212> TYPE: PRT
<213> ORGANISM: Artificial Sequence
<220> FEATURE:
<223> OTHER INFORMATION: GRS-EX-7

<400> SEQUENCE: 21

Ser Phe Gly Leu Gly Arg Ile Met Tyr Thr Val Phe Glu His Thr
1               5                   10                  15

<210> SEQ ID NO 22
<211> LENGTH: 13
<212> TYPE: PRT
<213> ORGANISM: Artificial Sequence
<220> FEATURE:
<223> OTHER INFORMATION: GRS-EX-8
```

<400> SEQUENCE: 22

Gly Arg Ile Met Tyr Thr Val Phe Glu His Thr Phe His
1               5                   10

<210> SEQ ID NO 23
<211> LENGTH: 20
<212> TYPE: PRT
<213> ORGANISM: Artificial Sequence
<220> FEATURE:
<223> OTHER INFORMATION: GRS-EX-9

<400> SEQUENCE: 23

Met Tyr Thr Val Phe Glu His Thr Phe His Val Arg Glu Gly Asp Glu
1               5                   10                  15

Gln Arg Thr Phe
            20

<210> SEQ ID NO 24
<211> LENGTH: 20
<212> TYPE: PRT
<213> ORGANISM: Artificial Sequence
<220> FEATURE:
<223> OTHER INFORMATION: GRS-EX-10

<400> SEQUENCE: 24

Asn Val Ile Glu Pro Ser Phe Gly Leu Gly Arg Ile Met Tyr Thr Val
1               5                   10                  15

Phe Glu His Thr
            20

<210> SEQ ID NO 25
<211> LENGTH: 17
<212> TYPE: PRT
<213> ORGANISM: Artificial Sequence
<220> FEATURE:
<223> OTHER INFORMATION: GRS-EX-11

<400> SEQUENCE: 25

Phe Gly Leu Gly Arg Ile Met Tyr Thr Val Phe Glu His Thr Phe His
1               5                   10                  15

Val

<210> SEQ ID NO 26
<211> LENGTH: 30
<212> TYPE: PRT
<213> ORGANISM: Artificial Sequence
<220> FEATURE:
<223> OTHER INFORMATION: GRS-EX-12

<400> SEQUENCE: 26

Leu Tyr Val Glu Glu Val Val Pro Asn Val Ile Glu Pro Ser Phe Gly
1               5                   10                  15

Leu Gly Arg Ile Met Tyr Thr Val Phe Glu His Thr Phe His
            20                  25                  30

<210> SEQ ID NO 27
<211> LENGTH: 35
<212> TYPE: PRT
<213> ORGANISM: Artificial Sequence
<220> FEATURE:
<223> OTHER INFORMATION: GRS-EX-14

<400> SEQUENCE: 27

Leu Gly Arg Ile Met Tyr Thr Val Phe Glu His Thr Phe His Val Arg

```
1               5                   10                  15

Glu Gly Asp Glu Gln Arg Thr Phe Phe Ser Phe Pro Ala Val Val Ala
            20                  25                  30

Pro Phe Lys
        35

<210> SEQ ID NO 28
<211> LENGTH: 50
<212> TYPE: PRT
<213> ORGANISM: Artificial Sequence
<220> FEATURE:
<223> OTHER INFORMATION: GRS-EX-19

<400> SEQUENCE: 28

Val Val Pro Asn Val Ile Glu Pro Ser Phe Gly Leu Gly Arg Ile Met
1               5                   10                  15

Tyr Thr Val Phe Glu His Thr Phe His Val Arg Glu Gly Asp Glu Gln
            20                  25                  30

Arg Thr Phe Phe Ser Phe Pro Ala Val Val Ala Pro Phe Lys Cys Ser
        35                  40                  45

Val Leu
    50

<210> SEQ ID NO 29
<211> LENGTH: 50
<212> TYPE: PRT
<213> ORGANISM: Artificial Sequence
<220> FEATURE:
<223> OTHER INFORMATION: GRS-EX-20

<400> SEQUENCE: 29

Met Tyr Thr Val Phe Glu His Thr Phe His Val Arg Glu Gly Asp Glu
1               5                   10                  15

Gln Arg Thr Phe Phe Ser Phe Pro Ala Val Val Ala Pro Phe Lys Cys
            20                  25                  30

Ser Val Leu Pro Leu Ser Gln Asn Gln Glu Phe Met Pro Phe Val Lys
        35                  40                  45

Glu Leu
    50

<210> SEQ ID NO 30
<211> LENGTH: 50
<212> TYPE: PRT
<213> ORGANISM: Artificial Sequence
<220> FEATURE:
<223> OTHER INFORMATION: GRS-EX-21

<400> SEQUENCE: 30

Phe Gly Leu Gly Arg Ile Met Tyr Thr Val Phe Glu His Thr Phe His
1               5                   10                  15

Val Arg Glu Gly Asp Glu Gln Arg Thr Phe Phe Ser Phe Pro Ala Val
            20                  25                  30

Val Ala Pro Phe Lys Cys Ser Val Leu Pro Leu Ser Gln Asn Gln Glu
        35                  40                  45

Phe Met
    50

<210> SEQ ID NO 31
<211> LENGTH: 50
<212> TYPE: PRT
<213> ORGANISM: Artificial Sequence
```

```
<220> FEATURE:
<223> OTHER INFORMATION: GRS-EX-22

<400> SEQUENCE: 31

Val Ile Glu Pro Ser Phe Gly Leu Gly Arg Ile Met Tyr Thr Val Phe
1               5                   10                  15

Glu His Thr Phe His Val Arg Glu Gly Asp Glu Gln Arg Thr Phe Phe
            20                  25                  30

Ser Phe Pro Ala Val Val Ala Pro Phe Lys Cys Ser Val Leu Pro Leu
        35                  40                  45

Ser Gln
    50

<210> SEQ ID NO 32
<211> LENGTH: 76
<212> TYPE: PRT
<213> ORGANISM: Artificial Sequence
<220> FEATURE:
<223> OTHER INFORMATION: GRS-EX-23

<400> SEQUENCE: 32

Gly Arg Ile Met Tyr Thr Val Phe Glu His Thr Phe His Val Arg Glu
1               5                   10                  15

Gly Asp Glu Gln Arg Thr Phe Phe Ser Phe Pro Ala Val Val Ala Pro
            20                  25                  30

Phe Lys Cys Ser Val Leu Pro Leu Ser Gln Asn Gln Glu Phe Met Pro
        35                  40                  45

Phe Val Lys Glu Leu Ser Glu Ala Leu Thr Arg His Gly Val Ser His
    50                  55                  60

Lys Val Asp Asp Ser Ser Gly Ser Ile Gly Arg Arg
65                  70                  75

<210> SEQ ID NO 33
<211> LENGTH: 100
<212> TYPE: PRT
<213> ORGANISM: Artificial Sequence
<220> FEATURE:
<223> OTHER INFORMATION: GRS-EX-25

<400> SEQUENCE: 33

Arg Ile Met Tyr Thr Val Phe Glu His Thr Phe His Val Arg Glu Gly
1               5                   10                  15

Asp Glu Gln Arg Thr Phe Phe Ser Phe Pro Ala Val Val Ala Pro Phe
            20                  25                  30

Lys Cys Ser Val Leu Pro Leu Ser Gln Asn Gln Glu Phe Met Pro Phe
        35                  40                  45

Val Lys Glu Leu Ser Glu Ala Leu Thr Arg His Gly Val Ser His Lys
    50                  55                  60

Val Asp Asp Ser Ser Gly Ser Ile Gly Arg Arg Tyr Ala Arg Thr Asp
65                  70                  75                  80

Glu Ile Gly Val Ala Phe Gly Val Thr Ile Asp Phe Asp Thr Val Asn
                85                  90                  95

Lys Thr Pro His
            100

<210> SEQ ID NO 34
<211> LENGTH: 120
<212> TYPE: PRT
<213> ORGANISM: Artificial Sequence
<220> FEATURE:
```

-continued

<223> OTHER INFORMATION: GRS-EX-27

<400> SEQUENCE: 34

```
Leu Tyr Val Glu Glu Val Val Pro Asn Val Ile Glu Pro Ser Phe Gly
1               5                   10                  15

Leu Gly Arg Ile Met Tyr Thr Val Phe Glu His Thr Phe His Val Arg
            20                  25                  30

Glu Gly Asp Glu Gln Arg Thr Phe Phe Ser Phe Pro Ala Val Val Ala
        35                  40                  45

Pro Phe Lys Cys Ser Val Leu Pro Leu Ser Gln Asn Gln Glu Phe Met
    50                  55                  60

Pro Phe Val Lys Glu Leu Ser Glu Ala Leu Thr Arg His Gly Val Ser
65                  70                  75                  80

His Lys Val Asp Asp Ser Ser Gly Ser Ile Gly Arg Arg Tyr Ala Arg
                85                  90                  95

Thr Asp Glu Ile Gly Val Ala Phe Gly Val Thr Ile Asp Phe Asp Thr
            100                 105                 110

Val Asn Lys Thr Pro His Thr Ala
        115                 120
```

<210> SEQ ID NO 35
<211> LENGTH: 150
<212> TYPE: PRT
<213> ORGANISM: Artificial Sequence
<220> FEATURE:
<223> OTHER INFORMATION: GRS-EX-28

<400> SEQUENCE: 35

```
Ile Met Tyr Thr Val Phe Glu His Thr Phe His Val Arg Glu Gly Asp
1               5                   10                  15

Glu Gln Arg Thr Phe Phe Ser Phe Pro Ala Val Val Ala Pro Phe Lys
            20                  25                  30

Cys Ser Val Leu Pro Leu Ser Gln Asn Gln Glu Phe Met Pro Phe Val
        35                  40                  45

Lys Glu Leu Ser Glu Ala Leu Thr Arg His Gly Val Ser His Lys Val
    50                  55                  60

Asp Asp Ser Ser Gly Ser Ile Gly Arg Arg Tyr Ala Arg Thr Asp Glu
65                  70                  75                  80

Ile Gly Val Ala Phe Gly Val Thr Ile Asp Phe Asp Thr Val Asn Lys
                85                  90                  95

Thr Pro His Thr Ala Thr Leu Arg Asp Arg Asp Ser Met Arg Gln Ile
            100                 105                 110

Arg Ala Glu Ile Ser Glu Leu Pro Ser Ile Val Gln Asp Leu Ala Asn
        115                 120                 125

Gly Asn Ile Thr Trp Ala Asp Val Glu Ala Arg Tyr Pro Leu Phe Glu
    130                 135                 140

Gly Gln Glu Thr Gly Lys
145                 150
```

<210> SEQ ID NO 36
<211> LENGTH: 170
<212> TYPE: PRT
<213> ORGANISM: Artificial Sequence
<220> FEATURE:
<223> OTHER INFORMATION: GRS-EX-29

<400> SEQUENCE: 36

```
Glu Val Val Pro Asn Val Ile Glu Pro Ser Phe Gly Leu Gly Arg Ile
```

-continued

```
1               5               10              15

Met Tyr Thr Val Phe Glu His Thr Phe His Val Arg Glu Gly Asp Glu
            20              25              30

Gln Arg Thr Phe Phe Ser Phe Pro Ala Val Val Ala Pro Phe Lys Cys
            35              40              45

Ser Val Leu Pro Leu Ser Gln Asn Gln Glu Phe Met Pro Phe Val Lys
            50              55              60

Glu Leu Ser Glu Ala Leu Thr Arg His Gly Val Ser His Lys Val Asp
65              70              75              80

Asp Ser Ser Gly Ser Ile Gly Arg Arg Tyr Ala Arg Thr Asp Glu Ile
                85              90              95

Gly Val Ala Phe Gly Val Thr Ile Asp Phe Asp Thr Val Asn Lys Thr
            100             105             110

Pro His Thr Ala Thr Leu Arg Asp Arg Asp Ser Met Arg Gln Ile Arg
            115             120             125

Ala Glu Ile Ser Glu Leu Pro Ser Ile Val Gln Asp Leu Ala Asn Gly
            130             135             140

Asn Ile Thr Trp Ala Asp Val Glu Ala Arg Tyr Pro Leu Phe Glu Gly
145             150             155             160

Gln Glu Thr Gly Lys Lys Glu Thr Ile Glu
                165             170

<210> SEQ ID NO 37
<211> LENGTH: 148
<212> TYPE: PRT
<213> ORGANISM: Artificial Sequence
<220> FEATURE:
<223> OTHER INFORMATION: GRS-F4-NT-2

<400> SEQUENCE: 37

Thr Phe His Val Arg Glu Gly Asp Glu Gln Arg Thr Phe Phe Ser Phe
1               5               10              15

Pro Ala Val Val Ala Pro Phe Lys Cys Ser Val Leu Pro Leu Ser Gln
            20              25              30

Asn Gln Glu Phe Met Pro Phe Val Lys Glu Leu Ser Glu Ala Leu Thr
            35              40              45

Arg His Gly Val Ser His Lys Val Asp Asp Ser Ser Gly Ser Ile Gly
        50              55              60

Arg Arg Tyr Ala Arg Thr Asp Glu Ile Gly Val Ala Phe Gly Val Thr
65              70              75              80

Ile Asp Phe Asp Thr Val Asn Lys Thr Pro His Thr Ala Thr Leu Arg
                85              90              95

Asp Arg Asp Ser Met Arg Gln Ile Arg Ala Glu Ile Ser Glu Leu Pro
            100             105             110

Ser Ile Val Gln Asp Leu Ala Asn Gly Asn Ile Thr Trp Ala Asp Val
            115             120             125

Glu Ala Arg Tyr Pro Leu Phe Glu Gly Gln Glu Thr Gly Lys Lys Glu
            130             135             140

Thr Ile Glu Glu
145

<210> SEQ ID NO 38
<211> LENGTH: 128
<212> TYPE: PRT
<213> ORGANISM: Artificial Sequence
<220> FEATURE:
<223> OTHER INFORMATION: GRS-F4-NT-3
```

<400> SEQUENCE: 38

Ala Pro Phe Lys Cys Ser Val Leu Pro Leu Ser Gln Asn Gln Glu Phe
1               5                   10                  15

Met Pro Phe Val Lys Glu Leu Ser Glu Ala Leu Thr Arg His Gly Val
            20                  25                  30

Ser His Lys Val Asp Asp Ser Ser Gly Ser Ile Gly Arg Arg Tyr Ala
        35                  40                  45

Arg Thr Asp Glu Ile Gly Val Ala Phe Gly Val Thr Ile Asp Phe Asp
        50                  55                  60

Thr Val Asn Lys Thr Pro His Thr Ala Thr Leu Arg Asp Arg Asp Ser
65                  70                  75                  80

Met Arg Gln Ile Arg Ala Glu Ile Ser Glu Leu Pro Ser Ile Val Gln
                85                  90                  95

Asp Leu Ala Asn Gly Asn Ile Thr Trp Ala Asp Val Glu Ala Arg Tyr
            100                 105                 110

Pro Leu Phe Glu Gly Gln Glu Thr Gly Lys Lys Glu Thr Ile Glu Glu
        115                 120                 125

<210> SEQ ID NO 39
<211> LENGTH: 6
<212> TYPE: PRT
<213> ORGANISM: Artificial Sequence
<220> FEATURE:
<223> OTHER INFORMATION: GRS-EX-0

<400> SEQUENCE: 39

Gly Leu Gly Arg Ile Met
1               5

<210> SEQ ID NO 40
<211> LENGTH: 25
<212> TYPE: PRT
<213> ORGANISM: Artificial Sequence
<220> FEATURE:
<223> OTHER INFORMATION: GRS-EX-13

<400> SEQUENCE: 40

Leu Tyr Val Glu Glu Val Val Pro Asn Val Ile Glu Pro Ser Phe Gly
1               5                   10                  15

Leu Gly Arg Ile Met Tyr Thr Val Phe
            20                  25

<210> SEQ ID NO 41
<211> LENGTH: 30
<212> TYPE: PRT
<213> ORGANISM: Artificial Sequence
<220> FEATURE:
<223> OTHER INFORMATION: GRS-EX-15

<400> SEQUENCE: 41

His Val Arg Glu Gly Asp Glu Gln Arg Thr Phe Phe Ser Phe Pro Ala
1               5                   10                  15

Val Val Ala Pro Phe Lys Cys Ser Val Leu Pro Leu Ser Gln
            20                  25                  30

<210> SEQ ID NO 42
<211> LENGTH: 130
<212> TYPE: PRT
<213> ORGANISM: Artificial Sequence
<220> FEATURE:
<223> OTHER INFORMATION: GRS-EX-16

<400> SEQUENCE: 42

Val Val Ala Pro Phe Lys Cys Ser Val Leu Pro Leu Ser Gln Asn Gln
1               5                   10                  15

Glu Phe Met Pro Phe Val Lys Glu Leu Ser Glu Ala Leu Thr Arg His
            20                  25                  30

Gly Val Ser His Lys Val Asp Asp Ser Ser Gly Ser Ile Gly Arg Arg
        35                  40                  45

Tyr Ala Arg Thr Asp Glu Ile Gly Val Ala Phe Gly Val Thr Ile Asp
    50                  55                  60

Phe Asp Thr Val Asn Lys Thr Pro His Thr Ala Thr Leu Arg Asp Arg
65                  70                  75                  80

Asp Ser Met Arg Gln Ile Arg Ala Glu Ile Ser Glu Leu Pro Ser Ile
            85                  90                  95

Val Gln Asp Leu Ala Asn Gly Asn Ile Thr Trp Ala Asp Val Glu Ala
            100                 105                 110

Arg Tyr Pro Leu Phe Glu Gly Gln Glu Thr Gly Lys Lys Glu Thr Ile
        115                 120                 125

Glu Glu
    130

<210> SEQ ID NO 43
<211> LENGTH: 15
<212> TYPE: PRT
<213> ORGANISM: Artificial Sequence
<220> FEATURE:
<223> OTHER INFORMATION: GRS-EX-17

<400> SEQUENCE: 43

Val Phe Glu His Thr Phe His Val Arg Glu Gly Asp Glu Gln Arg
1               5                   10                  15

<210> SEQ ID NO 44
<211> LENGTH: 10
<212> TYPE: PRT
<213> ORGANISM: Artificial Sequence
<220> FEATURE:
<223> OTHER INFORMATION: GRS-EX-18

<400> SEQUENCE: 44

Phe Gly Leu Gly Arg Ile Met Tyr Thr Val
1               5                   10

<210> SEQ ID NO 45
<211> LENGTH: 104
<212> TYPE: PRT
<213> ORGANISM: Artificial Sequence
<220> FEATURE:
<223> OTHER INFORMATION: GRS-EX-24

<400> SEQUENCE: 45

Val Lys Glu Leu Ser Glu Ala Leu Thr Arg His Gly Val Ser His Lys
1               5                   10                  15

Val Asp Asp Ser Ser Gly Ser Ile Gly Arg Arg Tyr Ala Arg Thr Asp
            20                  25                  30

Glu Ile Gly Val Ala Phe Gly Val Thr Ile Asp Phe Asp Thr Val Asn
        35                  40                  45

Lys Thr Pro His Thr Ala Thr Leu Arg Asp Arg Asp Ser Met Arg Gln
    50                  55                  60

Ile Arg Ala Glu Ile Ser Glu Leu Pro Ser Ile Val Gln Asp Leu Ala

-continued

```
65                70                75                80

Asn Gly Asn Ile Thr Trp Ala Asp Val Glu Ala Arg Tyr Pro Leu Phe
                85                90                95

Glu Gly Gln Glu Thr Gly Lys Lys
            100

<210> SEQ ID NO 46
<211> LENGTH: 37
<212> TYPE: PRT
<213> ORGANISM: Artificial Sequence
<220> FEATURE:
<223> OTHER INFORMATION: GRS-EX-26

<400> SEQUENCE: 46

Thr Val Phe Glu His Thr Phe His Val Arg Glu Gly Asp Glu Gln Arg
1               5                10                15

Thr Phe Phe Ser Phe Pro Ala Val Val Ala Pro Phe Lys Cys Ser Val
            20                25                30

Leu Pro Leu Ser Gln
            35
```

FRAGMENTED GRS POLYPEPTIDE AND VARIANT THEREOF, AND USE THEREOF

CROSS-REFERENCE TO RELATED APPLICATIONS

This application is a § 371 national phase of International Application No. PCT/KR2019/005849, filed on May 15, 2019, which claims the benefit of Korean Patent Application No. 10-2018-0058647, filed on May 23, 2018, which applications are incorporated by reference herein.

TECHNICAL FIELD

This application claims the benefit of priority to Korean Patent Application No. 10-2018-0058647, filed May 23, 2018, the content of which is incorporated herein by reference in its entirety.

The present invention relates to a fragmented GRS polypeptide, a variant thereof, and a use thereof. More particularly, the present invention relates to an isolated polypeptide consisting of 8 to 170 consecutive amino acids, which contains the amino acids from positions 531 to 538 of the amino acid sequence defined by SEQ ID NO: 1; or a variant having a sequence homology of 80% or more to the isolated polypeptide, a fusion protein comprising the polypeptide, and a complex comprising the polypeptide, a polynucleotide coding for the polypeptide, and uses thereof in preventing and treating a neoplastic disease, in detecting cancer cells, in imaging cancer cells, and in delivering a drug to cancer cells.

BACKGROUND ART

Aminoacyl-tRNA synthetase (ARS or AARS), which catalyzes the aminoacylation of tRNA molecules, is essential for decoding genetic information during the process of translation. Each of the eukaryotic tRNA synthetases consists of a core enzyme (closely related to the prokaryotic counterpart) and additional domains (appended to the amino- or carboxyl-terminal end of the core enzyme). Therefore, there is a significant difference in the constitution of the enzyme between eukaryotes and prokaryotes. For example, human tyrosyl-tRNA synthetase (TyrRS) has a carboxyl-terminal domain that is not part of prokaryotic and lower eukaryotic TyrRS molecules.

Several aminoacyl-tRNA synthetases have been recently demonstrated to have non-canonical functions distinct from their involvement in translation. That is, some fragments of ARS proteins were found to retain unpredictable activity irrelevant to aminoacylation, thus exhibiting extracellular signaling regulating pathways of different types beyond translation. Such unpredictable activities might often be therapeutically available for particular diseases, but in most cases, might have the risk of causing the onset of diseases in humans, rather. By way of example, lysyl-t-RNA synthetase (KRS) was identified to have the activity of promoting metastasis (Korean Patent No. 10-1453141). In addition, mini-tyrosyl tRNA synthetase (mini-TRS), which is the N-terminal domain (corresponding to amino acid residues 1-364) of TyrRS which is cleaved by polymorphonuclear cell elastase and plasmin, exhibits a non-canonical biological activity which is not found in the full-length protein. In vitro, mini-TyrRS has been shown to stimulate endothelial cell proliferation and migration (Wakasugi et al., Proc. Natl. Acad. Sci. 99: 173-177 (2002)) and to be pro-angiogenic in mouse matrigel assays. Generally, the function of promoting angiogenesis is closely related to cancer metastasis.

Such unpredicted activity may be not observed in natural full-length amino acid sequences (or show only insignificant effects at full-length protein levels), but may be prominent in truncated forms. In addition, specific activities in truncated proteins may retain therapeutically improper properties. In order to overcome the problem with the unpredictability and utilize therapeutic potentials of this family of proteins, there is a need to identify biologically relevant forms of other aminoacyl-tRNA synthetase proteins In the pharmaceutical industry, there has been a trend toward a development change from natural products or chemical synthetic medications in the past to protein or peptide drugs. In the world market of drugs, the market size of protein or peptide drugs expanded from 43.7 billion dollars in 2006 to 88.5 billion dollars in 2011. The Korean domestic protein drug market accounts for 3% of the world market in 2006, with the anticipation of expansion to 7% in 2021. Protein or peptide drugs have been evaluated as innovations in pharmaceuticals because they have fewer side effects and are more effective than synthetic drugs.

Currently, the importance of biomedicines in the pipeline of major pharmaceutical companies is increasing, but there are major technical problems until the launch of certain biomedicines such as peptides. For example, low delivery rates to target sites, long-chain peptide synthesis, etc. are obstacles to commercialization. Generally, peptides are made up of about 50 amino acids or less. The key to a success as peptide drugs depends on the exploitation of short-chain and active peptides, that is, excavation of minimum units (motifs) having a biological activity from full-length proteins. Long peptides require high production costs, are not easy to synthesize, and exhibit problematic body uptake.

When a protein is observed to have a novel activity that has not yet been reported in the family of the protein, it is a hard task with significant difficulty to find out a biologically active motif responsible for the novel activity (Salma Aouled El Haj Mohamed et al., Motif Discovery in Protein Sequences, Pattern Recognition—Analysis and Applications, Dec. 14, 2016, pp. 1-134).

DETAILED DESCRIPTION OF THE INVENTION

Technical Problem

The present inventors identified the cancer cell killing activity of GRS (glycyl-tRNA synthetase) protein and first revealed a domain and a core motif which each retain the anticancer activity of GRS. Thorough and intensive research, conducted by the present inventors, resulted in the finding that a GRS polypeptide fragment containing the motif, constructed to a predetermined length, and variants thereof are far superior to the full-length protein and the domain unit in terms of cancer killing activity, leading to the present invention.

It is therefore a purpose of the present invention to provide a polypeptide comprising: an isolated polypeptide consisting of consecutive 8 to 170 amino acid residues, which contains amino acids at positions 531 to 538 of the amino acid sequence defined by SEQ ID NO: 1; or a variant having a sequence homology of 80% or more with the isolated polypeptide.

It is another purpose of the present invention to provide a PEGylated form of the polypeptide.

It is another purpose of the present invention to provide a fusion protein including the polypeptide and a heterologous fusion partner.

It is another purpose of the present invention to provide a dimeric or multimeric complex including at least one of the polypeptide.

It is another purpose of the present invention to provide a polynucleotide encoding the polypeptide.

It is another purpose of the present invention to provide an expression vector comprising the polynucleotide.

It is another purpose of the present invention to provide a host cell comprising the expression vector.

It is another purpose of the present invention to provide a composition comprising a physiologically acceptable carrier and at least one selected from the group consisting of:

(i) the polypeptide of the present invention, (ii) a fusion protein comprising the polypeptide of (i) and heterologous fusion partner, (iii) a dimeric or multimeric complex comprising at least one polypeptide of (i), (iv) a polynucleotide encoding (i) to (iii), (v) an expression vector comprising (iv), and (vi) a host cell comprising (v).

It is another purpose of the present invention to provide a pharmaceutical composition comprising the polypeptide or the polynucleotide as an active ingredient for prevention or treatment of a neoplastic disease.

It is another purpose of the present invention to provide a pharmaceutical composition consisting of the polypeptide or the polynucleotide as an active ingredient for prevention or treatment of a neoplastic disease.

It is another purpose of the present invention to provide a pharmaceutical composition consisting essentially of the polypeptide or the polynucleotide as an active ingredient for prevention or treatment of a neoplastic disease.

It is another purpose of the present invention to provide a screening method for identifying an anticancer agent, the method comprising the steps of:

(a) forming a reaction mixture containing (i) and (ii):

(i) an ingredient selected from the group consisting of the polypeptide and the polynucleotide of the present invention, and (ii) a test compound; and (b) determining an increase in an anti-cancer activity by the ingredient in the presence of the test compound, wherein a change in the anti-cancer activity in the presence of the test compound is determined compared to the anti-cancer activity in the absence of the test compound, thereby identifying an active test compound.

It is another purpose of the present invention to provide a composition comprising the polypeptide as an active ingredient for detecting or imaging cancer cells.

It is another purpose of the present invention to provide a composition consisting of the polypeptide as an active ingredient for detecting or imaging cancer cells.

It is another purpose of the present invention to provide a composition consisting essentially of the polypeptide as an active ingredient for detecting or imaging cancer cells.

It is another purpose of the present invention to provide a method for detecting cancer cells, the method comprising the steps of: (a) mixing the polypeptides with a biological sample; (b) removing the polypeptides that remain unbound or are non-specifically bound; and (C) determining whether and where the polypeptides are bound.

It is another purpose of the present invention to provide a composition comprising the polypeptide as an active ingredient for a cancer cell-specific drug delivery.

It is another purpose of the present invention to provide a composition consisting of the polypeptide as an active ingredient for a cancer cell-specific drug delivery.

It is another purpose of the present invention to provide a composition consisting essentially of the polypeptide as an active ingredient for a cancer cell-specific drug delivery.

It is another purpose of the present invention to provide a composition comprising the polypeptide and an anticancer agent bound thereto as active ingredients for prevention and treatment of cancer.

It is another purpose of the present invention to provide a composition consisting of the polypeptide and an anticancer agent bound thereto as active ingredients for prevention and treatment of cancer.

It is another purpose of the present invention to provide a composition consisting essentially of the polypeptide and an anticancer agent bound thereto as active ingredients for prevention and treatment of cancer.

It is another purpose of the present invention to provide a use of the polypeptide or the polynucleotide in preparing an agent for prevention and treatment of a neoplastic disease.

It is another purpose of the present invention to provide a method for prevention and treatment of a neoplastic disease, the method comprising a step of administering to a subject in need thereof an effective amount of a composition comprising the polypeptide or the polynucleotide as an active ingredient.

It is another purpose of the present invention to provide a use of the polypeptide in preparing an agent for detecting cancer cells, an agent for imaging cancer cells, or an agent for delivery of a cancer cell-specific drug.

It is another purpose of the present invention to provide method for imaging cancer cells or for cancer cell-specific drug delivery, the method comprising a step of administering to a subject in need thereof an effective amount of a composition comprising the polypeptide as an active ingredient.

It is another purpose of the present invention to provide a use of the polypeptide and an anticancer agent bound thereto in preparing an agent for prevention and treatment of cancer.

It is another purpose of the present invention to provide a method for prevention or treatment of cancer, the method comprising a step of administering to a subject in need thereof an effective amount of a composition comprising the polypeptide and an anticancer agent bound thereto.

Technical Solution

In order to accomplish the purpose described above, the present invention provides a polypeptide comprising: an isolated polypeptide consisting of consecutive 8 to 170 amino acid residues, which contains amino acids at positions 531 to 538 of the amino acid sequence defined by SEQ ID NO: 1; or a variant having a sequence homology of 80% or more with the isolated polypeptide.

In order to accomplish another purpose, the present invention provides a PEGylated form of the polypeptide.

In order to accomplish another purpose, the present invention provides a fusion protein comprising the polypeptide and a heterologous fusion partner.

In order to accomplish another purpose, the present invention provides a dimeric or multimeric complex comprising at least one of the polypeptide.

In order to accomplish another purpose, the present invention provides a polynucleotide encoding the polypeptide.

In order to accomplish another purpose, the present invention provides an expression vector comprising the polynucleotide.

In order to accomplish another purpose, the present invention provides a host cell comprising the expression vector.

In order to accomplish another purpose, the present invention provides a composition comprising a physiologically acceptable carrier and at least one selected from the group consisting of:

(i) the polypeptide of the present invention, (ii) a fusion protein comprising the polypeptide of (i) and heterologous fusion partner, (iii) a dimeric or multimeric complex comprising at least one polypeptide of (i), (iv) a polynucleotide encoding (i) to (iii), (v) an expression vector comprising (iv), and (vi) a host cell comprising (v).

In order to accomplish another purpose, the present invention provides a pharmaceutical composition comprising the polypeptide or the polynucleotide as an active ingredient for prevention or treatment of a neoplastic disease.

In order to accomplish another purpose, the present invention provides a pharmaceutical composition consisting of the polypeptide or the polynucleotide as an active ingredient for prevention or treatment of a neoplastic disease.

In order to accomplish another purpose, the present invention provides a pharmaceutical composition consisting essentially of the polypeptide or the polynucleotide as an active ingredient for prevention or treatment of a neoplastic disease.

In order to accomplish another purpose, the present invention provides a screening method for identifying an anticancer agent, the method comprising the steps of:

(a) forming a reaction mixture containing (i) and (ii):

(i) an ingredient selected from the group consisting of the polypeptide and the polynucleotide of the present invention, (ii) a test compound; and (b) determining an increase in an anti-cancer activity by the ingredient in the presence of the test compound, wherein a change in the anti-cancer activity in the presence of the test compound is determined compared to the anti-cancer activity in the absence of the test compound, thereby identifying an active test compound.

In order to accomplish another purpose, the present invention provides a composition comprising the polypeptide as an active ingredient for detecting or imaging cancer cells.

In order to accomplish another purpose, the present invention provides a composition consisting of the polypeptide as an active ingredient for detecting or imaging cancer cells.

In order to accomplish another purpose, the present invention provides a composition consisting essentially of the polypeptide as an active ingredient for detecting or imaging cancer cells.

In order to accomplish another purpose, the present invention provides a method for detecting cancer cells, the method comprising the steps of: (a) mixing the polypeptides with a biological sample; (b) removing the polypeptides that remain unbound or are non-specifically bound; and (c) determining whether and where the polypeptides are bound.

In order to accomplish another purpose, the present invention provides a composition comprising the polypeptide as an active ingredient for cancer cell-specific drug delivery.

In order to accomplish another purpose, the present invention provides a composition consisting of the polypeptide as an active ingredient for cancer cell-specific drug delivery.

In order to accomplish another purpose, the present invention provides a composition consisting essentially of the polypeptide as an active ingredient for cancer cell-specific drug delivery.

In order to accomplish another purpose, the present invention provides a composition comprising the polypeptide and an anticancer agent bound thereto as active ingredients for prevention and treatment of cancer.

In order to accomplish another purpose, the present invention provides a composition consisting of the polypeptide and an anticancer agent bound thereto as active ingredients for prevention and treatment of cancer.

In order to accomplish another purpose, the present invention provides a composition consisting essentially of the polypeptide and an anticancer agent bound thereto as active ingredients for prevention and treatment of cancer.

In order to accomplish another purpose, the present invention provides a use of the polypeptide or the polynucleotide in preparing an agent for prevention and treatment of a neoplastic disease.

In order to accomplish another purpose, the present invention provides a method for prevention and treatment of a neoplastic disease, the method comprising a step of administering to a subject in need thereof an effective amount of a composition comprising the polypeptide or the polynucleotide as an active ingredient.

In order to accomplish another purpose, the present invention provides a use of the polypeptide in preparing an agent for detecting cancer cells, an agent for imaging cancer cells, or an agent for cancer cell-specific delivery of a drug.

In order to accomplish another purpose, the present invention provides a method for imaging cancer cells or for cancer cell-specific delivery of a drug, the method comprising a step of administering to a subject in need thereof an effective amount of a composition comprising the polypeptide as an active ingredient.

In order to accomplish another purpose, the present invention provides a use of the polypeptide and an anticancer agent bound thereto in preparing an agent for prevention and treatment of cancer.

In order to accomplish another purpose, the present invention provides a method for prevention or treatment of cancer, the method comprising a step of administering to a subject in need thereof an effective amount of a composition comprising the polypeptide and an anticancer agent bound thereto.

Hereinafter, the present invention will be explained in detail.

The practice of the present invention will employ, unless indicated specifically to the contrary, conventional methods of molecular biology and recombinant DNA techniques within the skill of the art, many of which are described below for the purpose of illustration.

All publications, patents, and patent applications cited herein are hereby incorporated by reference in their entirety.

Throughout this application, various embodiments or conditions of this invention may be presented in a range format. Unless stated otherwise, a range value in the description means including the corresponding boundary values, that is, all values from the lower limit to the upper limit. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 7 to 170 should be considered to have specifically disclosed subranges such as from 10 to 127, from 23 to 35, from 80 to 100, from 50 to 169, etc., as well as individual numbers within that range, for example, 9, 27, 35, 101, and 155. This applies regardless of the breadth of the range.

The term "comprising" of the present invention is used synonymously with "containing" or "characterized in that" and does not exclude additional component elements or method steps not mentioned in the composition or method. The term "consisting of" refers to excluding additional elements, steps or components not otherwise mentioned. The term "consisting essentially of" is intended to encompass component elements or steps, etc., which, in addition to the described component elements or steps, do not substantially affect their underlying properties.

As used herein, the singular form "a", "an", and "the" include plural references unless the context clearly dictates otherwise. For example, the term "a compound" or "at least one compound" may include a plurality of compounds, including mixtures thereof.

The term "polypeptide" or "protein", is used in its conventional meaning, i.e., as a sequence of amino acids. The polypeptides are not limited to a specific length of the product, but refer generally to fragments of full-length proteins in the context of the present invention. This term is also intended to encompass post-expression modifications of the polypeptide, for example, glycosylations, acetylations, phosphorylations, and the like, as well as other modifications known in the art (both naturally occurring and non-naturally occurring). The polypeptides and proteins of the present invention may be prepared using any various recombinant and/or synthesis techniques known in the art, the exemplary embodiments of which will be additionally described below.

As described herein, "(single letter for an amino acid) (amino acid position) (single letter for another amino acid)" means that the former amino acid at the corresponding amino acid position of the original polypeptide (e.g., the full-length GRS sequence in this application) is substituted with the latter amino acid. For example, E536D means that the glutamine residue at position 536 on the wild-type polypeptide sequence (GRS of SEQ ID NO: 1) is substituted with aspartic acid.

Observations of non-canonical and therapeutically relevant activities associated with glycyl-tRNA synthetase (GRS) and GRS-derived specific polypeptides lead to the present invention.

"Non-canonical activity", as used herein, refers generally to an activity possessed by a GRS polypeptide of the invention that is other than the addition of glycine onto a tRNA molecule. As described herein, in certain embodiments, a non-canonical biological activity exhibited by a GRS polypeptide of the invention may include, but is not limited to, modulation of cell proliferation, modulation of apoptosis, modulation of cell migration, modulation of cellular signaling, and/or modulation of cytokine production and/or secretion. In a concrete embodiment, the activity may include modulation of Akt-mediated cellular signaling, modulation of Erk1/2-mediated cellular signaling, and modulation of GPCR-mediated cellular signaling, modulation of endothelial cell tube formation, and modulation of cell binding. In another embodiment, the activity may include modulation of CD71 and/or CD80. In another embodiment, the activity may include modulation of cytokine production and/or release, wherein the cytokine may be selected from the group consisting of TNF-α, IL1-β, IL-6, IL-8, IL-10, IL-12p40, MIP1-α, MIP-1β, GRO-α, MCP-1, and IL-1ra.

According to an aspect thereof, the present invention provides not only an isolated GRS polypeptide having at least one non-canonical, biological activity, but also an active fragment and a variant thereof which both substantially retain the non-canonical activity.

In detail, the present inventors showed that the GRS (glycyl-tRNA synthetase) can induce apoptosis of tumor cells by suppressing ERK signaling through dephosphorylation of ERK (Park M C, et al. (2012) Secreted human glycyl-tRNA synthetase implicated in defense against ERK-activated tumorigenesis. Proc Natl Acad Sci USA 109(11): E640-647.). Briefly, glycyl-tRNA synthetase (GRS) is secreted from macrophages and binds to cadherin-6 (CDH6) expressed on tumor cells. GRS binds to CDH6 and releases phosphatase 2A (PP2A) from CDH6. ERK signaling is involved in the growth of tumor cells. The released PP2A then suppresses ERK signaling through dephosphorylation of ERK and induces apoptosis of tumor cells.

Subsequently, the present inventors revealed that a protein region covering 511$^{th}$ to 685$^{th}$ amino acid residues on the amino acid sequence of GRS protein (SEQ ID NO: 1) is a domain (hereinafter referred to as "GRS-F4") having apoptotic activity against tumor (cancer) cells, first reporting that a motif essentially responsible for the cell apoptotic activity is a region ranging from the 532$^{nd}$ to the 538$^{th}$ amino acid residue on the amino acid sequence of GRS protein. It was also found that polypeptide fragments that have predetermined lengths and contain the motif and variants thereof are far remarkably superior to conventional proteins and domains in terms of activity. The core motif for GRS anticancer activity is first disclosed in the present invention.

Therefore, the present invention provides an isolated polypeptide consisting of 8 to 170 consecutive amino acid residues, which contains amino acids at positions 531 to 538 of the amino acid sequence defined by SEQ ID NO: 1; or
a variant having a sequence homology of 80% or more with the isolated polypeptide.

In addition, the present invention provides an isolated polypeptide consisting of 8 to 170 consecutive amino acid residues, which essentially contains amino acids at positions 531 to 538 on the amino acid sequence defined by SEQ ID NO: 1; or
a variant having a sequence homology of 80% or more with the isolated polypeptide In a particular embodiment thereof, the present invention provides an isolated polypeptide consisting of 7 to 170 consecutive amino acid residues, which contains amino acids at positions 532 to 538 of the amino acid sequence defined by SEQ ID NO: 1; or
a variant having a sequence homology of 80% or more with the isolated polypeptide.

In addition, the present invention provides an isolated polypeptide consisting of 7 to 170 consecutive amino acid residues, which essentially contains amino acids at positions 532 to 538 of the amino acid sequence defined by SEQ ID NO: 1; or
a variant having a sequence homology of 80% or more with the isolated polypeptide.

As used herein, the term "isolated polypeptide" means a truncated form of GRS protein. The isolated GRS polypeptide of the present invention is a consecutive fragment of the full-length human GRS protein. In a further particular embodiment, the GRS polypeptide is a consecutive fragment on the amino acid sequence of human GRS protein defined by SEQ ID NO: 1.

The fragment may be arbitrary in length and may also maintain (retain) at least one non-canonical biological activity of interest. In detail, so long as the isolated GRS polypeptide of the present invention consists of 7 to 170 consecutive amino acids, which contains the amino acids from positions 532 to 538 (hereinafter referred to as "cell apoptotic motif") on the amino acid sequence defined by SEQ ID NO: 1, any sequence length may be given thereto. More particularly, so long as the isolated GRS polypeptide of the present invention consists of 8 to 170 consecutive amino acids, which contains the amino acids from positions 531 to 538 on the amino acid sequence defined by SEQ ID NO: 1, any sequence length may be given thereto.

The isolated polypeptide of the present invention comprises, as a cell apoptotic motif, an amino acid region covering positions 532 to 538 on the amino acid sequence defined by SEQ ID NO: 1. More particularly, the isolated polypeptide of the present invention comprises an amino acid region covering positions 531 to 538 on the amino acid sequence defined by SEQ ID NO: 1. In an embodiment of the present invention, the exemplary polypeptides GRS-DP-B (SEQ ID NO: 2) GRS-DP-A linear (SEQ ID NO: 3, GRS 531-555 aa), GRS-DP (SEQ ID NO: 4, GRS 531-600 aa), and GRS-F4-NT-1 (SEQ ID NO: 6, GRS 526-685 aa), which are representative of the various polypeptides suggested in the present invention, were assayed for anticancer activity and targeting ability and the assay results were depicted. As a result, GRS-DP-B was found to comprise an important active motif. Accordingly, it was reported that so long as it contains the motif, any fragment can achieve the non-canonical, biological activity (particularly, cell apoptotic activity) intended by the present invention. Moreover, GRS-DP-B polypeptide was observed to have an excellent effect of specifically targeting cancer cells. Therefore, any fragment that contains the GRS-DP-B region can achieve a significant level of cancer cell targeting as the present invention intends.

According to the embodiments, it may be understood that the isolated polypeptide of the present invention comprises amino acid residues at positions 526 to 685, 531 to 685, 531 to 600, 531 to 555, or 531 to 538 on the amino acid sequence defined by SEQ ID NO: 1. In other words, the isolated polypeptide of the present invention comprises an amino acid sequence selected from the group consisting of SEQ ID NOS: 2 to 6.

Particularly, the isolated polypeptide of the present invention may consist essentially of an amino acid sequence selected from the group consisting of SEQ ID NOS: 2 to 6 and SEQ ID NOS: 15 to 36. More particularly, the isolated polypeptide of the present invention may consist of an amino acid sequence selected from the group consisting of SEQ ID NOS: 2 to 6 and SEQ ID NOS: 15 to 36.

In view of polypeptide length, the isolated polypeptide of the present invention may consist of 7 to 160 consecutive amino acids containing the cell apoptotic motif. More particularly, the isolated polypeptide of the present invention may consist of 7 to 100 consecutive amino acids containing the cell apoptotic motif. Furthermore, the isolated polypeptide of the present invention may consist of 7 to 50 consecutive amino acids containing the cell apoptotic motif. The number of the amino acids that serve as members of the isolated polypeptide of the present invention may be, for example, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 110, 115, 120, 125, 130, 135, 140, 145, 150, 155, 160, 165, or 170, with the cell apoptotic motif included therein.

More particularly, the isolated polypeptide of the present invention may consist of 7 to 20 consecutive amino acids containing the cell apoptotic motif. More particularly, the isolated polypeptide of the present invention may consist of 7 to 10 consecutive amino acids containing the cell apoptotic motif.

In a more particular embodiment, the isolated polypeptide of the present invention may consist of 8 to 160 consecutive amino acids containing the cell apoptotic motif. More particularly, the isolated polypeptide of the present invention may consist of 8 to 100 consecutive amino acids containing the cell apoptotic motif. More particularly, the isolated polypeptide of the present invention may consist of 8 to 50 consecutive amino acids containing the cell apoptotic motif.

More particularly, the isolated polypeptide of the present invention may consist of 8 to 20 consecutive amino acids containing the cell apoptotic motif. More particularly, the isolated polypeptide of the present invention may consist of 8 to 10 consecutive amino acids containing the cell apoptotic motif.

The "isolated polypeptide", i.e., "truncated GRS polypeptide" in the present invention can be prepared using an available technique known in the art. For example, it can be prepared using various proteases. Concrete examples of proteases include achromopeptidase, aminopeptidase, ancrod, angiotensin converting enzyme, bromelain, calpain, calpain I, calpain II, carboxypeptidase A, carboxypeptidase B, carboxypeptidase G, carboxypeptidase P, carboxypeptidase W, carboxypeptidase Y, caspase 1, caspase 2, caspase 3, caspase 4, caspase 5, caspase 6, caspase 7, caspase 8, caspase 9, caspase 10, caspase 11, caspase 12, caspase 13, cathepsin B, cathepsin C, cathepsin D, cathepsin E, cathepsin G, cathepsin H, cathepsin L, chymopapain, chymase, chymotrypsin, clostripain, collagenase, complement Clr, complement C1s, complement factor D, complement factor I, cucumisin, dipeptidyl peptidase IV, elastase, leukocyte, elastase, pancreatic, endoproteinase Arg-C, endoproteinase Asp-N, endoproteinase Glu-C, endoproteinase Lys-C, enterokinase, factor Xa, ficin, furin, granzyme A, granzyme B, HIV Protease, IGase, kallikrein tissue, leucine aminopeptidase (general), leucine aminopeptidase (cytosol), leucine aminopeptidase (microsomal), matrix metalloprotease, methionine aminopeptidase, neutrase, papain, pepsin, plasmin, prolidase, pronase E, prostate specific antigen, protease alkalophilic from *Streptomyces griseus*, protease from *Aspergillus*, protease from *Aspergillus saitoi*, protease from *Aspergillus sojae*, protease *B. licheniformis* (alkaline or alcalase), protease from *Bacillus polymyxa*, protease from *Bacillus* sp., protease from *Rhizopus* sp., protease S, proteasomes, proteinase from *Aspergillus oryzae*, proteinase 3, proteinase A, proteinase K, protein C, pyroglutamate aminopeptidase, rennin, streptokinase, subtilisin, thermolysin, thrombin, tissue plasminogen activator, trypsin, tryptase, and urokinase. In consideration of chemical specificity of a fragment to be constructed, a person skilled in the art could easily determine which protease is proper.

The polypeptides described herein may be prepared using any suitable procedure known to a person skilled in the art, such as by recombinant techniques. In addition to a recombinant technique, polypeptides of the present invention may be produced by a direct peptide synthesis method using solid phase techniques (Merrifield, J. Am. Chem. Soc. 85:2149-2154 (1963)).

Solid-phase peptide synthesis (SPPS) methods can initiate synthesis by attaching functional units, called linkers, to small porous beads on which peptide chains are induced to be built. Unlike the liquid phase method, the peptides covalently bind to the beads to prevent them from falling off by filtration until the nascent chains are cleaved by certain reactants such as trifluoroacetic acid (TFA). SPPS is achieved by repeating cycles of: protection in which the free N-terminal amine of a peptide immobilized onto a solid phase is coupled to a N-protected amino acid unit; deprotection; and coupling in which a new revealed free N-terminal amine is re-coupled to a further amino acid unit (deprotection-wash-coupling-wash). SPPS methods may be conducted with the aid of microwave irradiation. By applying thermal energy during the peptide synthesis process, the microwave-assisted peptide synthesis can reduce the time required for coupling and deprotection in each cycle. The thermal energy can prevent the extending peptide chains to folding or aggregating and can promote the chemical bonding.

In addition, the peptides of the present invention can be synthesized using a solid-phase peptide synthesis method. As for the concrete processes, reference may be made to the following literature: U.S. Pat. No. 5,516,891. Furthermore, peptides of the present invention may be synthesized by various methods such as a combination of solid- and liquid-phase synthesis methods, and the preparation is not limited to the methods described herein.

Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the desired molecule.

The polypeptides of the present invention comprise GRS variants having a sequence homology of 80% or more with the isolated polypeptides from GRS. As used herein, the term "GRS variant" refers to an active variant of the isolated polypeptide fragment, wherein the active variant retains at least one desired non-canonical activity (i.e., cell apoptotic activity) from the origin polypeptide thereof. In an embodiment, the variant of the present invention, whether naturally occurring or artificially generated, may be a splice variant which has at least one non-canonical activity described herein. In another embodiment, the variant, whether naturally occurring or artificially generated, comprises at least one point mutation against the wild-type GRS polypeptide and the mutant polypeptide retains, for example, at least one non-canonical activity described herein. That is, the variant (or term "active variant") is understood to be a functional equivalent of the "isolated polypeptide".

More specifically, the variant (GRS variant) is a functional equivalent having a sequence homology of at least 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more to any of the "isolated (GRS) polypeptide" sequences described above, along the length thereof.

In an embodiment of the present invention, variants constructed from the isolated polypeptides were assayed for activity, and especially, GRS-DP-A cyclic variant (SEQ ID NO: 7, variant of GRS-DP-A linear) was shown to have excellent apoptotic activity against cancer cells. Accordingly, given a sequence homology of 80% or more, the isolated GRS polypeptide fragments of the present invention can exhibit the desired non-canonical biological activity (particularly, cell apoptotic activity) desired in the present invention. In addition, variants such as GRS-DP-A cyclic was identified to have remarkable cancer cell-targeting ability.

In an embodiment, the variant of the present invention may comprise a sequence having a sequence homology of 80% or more to the amino sequence from positions 526 to 685, 531 to 685, 531 to 600, 531 to 555, or 531 to 538 on the amino acid sequence defined by SEQ ID NO: 1. In other words, the variant may comprise a sequence having a sequence homology of 80% or more to one amino acid sequence selected from the group consisting of SEQ ID NOS: 2 to 6.

Particularly, the variant of the present invention may consist essentially of a sequence having a sequence homology of 80% or more to any one selected from the group consisting of SEQ ID NOS: 2 to 6 and SEQ ID NOS: 15 to 36. More particularly, the isolated GRS polypeptide of the present invention may consist of a sequence having a sequence homology of 80% or more to any amino acid sequence selected from the group consisting of SEQ ID NOS: 2 to 6 and SEQ ID NOS: 15 to 36.

Most particularly, the variant of the present invention may be a polypeptide comprising an amino acid sequence defined by SEQ ID NO: 7, or a polypeptide consisting essentially of an amino acid sequence defined by SEQ ID NO: 7, and more particularly, a polypeptide consisting of an amino acid sequence defined by SEQ ID NO: 7.

The variant results from any modification in the "isolated polypeptide", which may be at least one substitution, deletion, addition, and/or insertion. The variant may be a naturally-occurring mutant or may be synthetically produced by, for example, changing or modifying at least one of the polypeptide sequences of the present invention and assaying the same for biological activity.

In certain embodiments, a variant will contain conservative substitutions. A "conservative substitution" is one in which an amino acid is substituted for another amino acid that has similar properties, such that one skilled in the art would expect the secondary structure and hydropathic nature (hydrophobicity or hydrophilicity) of the polypeptide to be substantially unchanged. Examples of conservative substitutions of naturally occurring amino acids are as follows: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved variant of a GRS polypeptide of the invention, a person skilled in the art, for example, can change one or more of the codons on the basis of the protein codon information known in the art.

Certain amino acids may be substituted for other amino acids in a protein structure without appreciable loss of interactive binding capacity with structures such as, for example, antigen-binding regions of antibodies, binding sites on substrate molecules, and such like. Since it is the interactive capacity and nature of a protein that generally defines that protein's biological functional activity, certain amino acid sequence substitutions can be made in a protein sequence, and, of course, its underlying DNA coding sequence, but nevertheless obtain a protein with like properties.

It is thus contemplated that various changes may be made in the polypeptide sequences of the disclosed compositions, or corresponding DNA sequences which encode the polypeptides without appreciable loss of their desired utility or activity. In making such changes, the hydropathic (hydrophobic or hydrophilic) index of amino acids may also be considered. The importance of the hydropathic amino acid index in conferring interactive biologic function on a protein is generally understood in the art (Kyte and Doolittle, 1982, incorporated herein by reference). For example, it is known that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity (i.e. still obtain a biological functionally equivalent protein). In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid can be substituted for another having a similar hydrophilicity value and still obtain a biologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine, and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine, and tyrosine.

In certain embodiments, a variant will contain conservative substitutions. A "conservative substitution" is one in which an amino acid is substituted for another amino acid that has similar properties, such that one skilled in the art would expect the secondary structure and hydropathic nature (hydrophobicity or hydrophilicity) of the polypeptide to be substantially unchanged. Examples of conservative substitutions of naturally occurring amino acids are as follows: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

The variant may also, or alternatively, contain non-conservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on secondary structure and hydropathic nature of the polypeptide.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to 75, 40 to 50, in which a sequence may be compared to a reference sequence of the same number of contiguous positions after the two sequences are optimally aligned.

Optimal alignment of sequences for comparison may be conducted, for example, using the Megalign program in the Lasergene suite of bioinformatics software (DNASTAR, Inc., Madison, Wis.), using default parameters.

Alternatively, optimal alignment of sequences for comparison may be conducted by the local identity algorithm, by the identity alignment algorithm, by the search for similarity methods, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

Examples of algorithms that are suitable for determining percent sequence identity and sequence similarity are the BLAST and BLAST 2.0 algorithms. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score.

Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one illustrative approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5-15 percent, or 10-12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

As the polypeptides provided by the present invention, the isolated polypeptides from GRS, or variants thereof may be in a linear form or a cyclic form, which can be understood with reference to Examples described herein.

The construction of a cyclic peptide as the variant of the present invention can be achieved using any well-known peptide cyclization method, without particular limitations to concrete cyclization processes and resulting cyclization forms. Preferably, the construction of a cyclic peptide of the present invention may be carried out by making a cleavage or substitution on a linear peptide so as to locate a cysteine residue at each of the opposite termini (N- and C-terminus) and allowing the formation of a monosulfide bond between two cysteine residues at both terminals.

Certain embodiments of the present invention also contemplate the use of modified polypeptides, including modifications that improve desired characteristics of the polypeptide (the isolated polypeptide or a variant thereof), as described herein. Illustrative modifications of the polypeptides of the invention include, but are not limited to, chemical and/or enzymatic derivatizations at one or more constituent amino acids, including side chain modifications, backbone modifications, and N- and/or C-terminal modifications including acetylation, hydroxylation, methylation, amidation, and the attachment of carbohydrate or lipid moieties, cofactors, and the like. Exemplary modifications also include pegylation of the polypeptide.

In certain aspects, chemoselective ligation technology may be utilized to modify polypeptides of the invention, such as by attaching polymers in a site-specific and controlled manner. Such technology typically relies on the incorporation of chemoselective anchors into the protein backbone by either chemical or recombinant means and subsequent modification with a polymer carrying a complementary linker. As a result, the assembly process and the covalent structure of the resulting protein-polymer conjugate may be controlled, enabling the rational optimization of drug properties, such as efficacy and pharmacokinetic properties.

Particularly, the present invention provides a PEGylated form of the polypeptide of the present invention.

PEG is a well-known polymer having the properties of solubility in water and in many organic solvents, lack of toxicity, and lack of immunogenicity. It is also clear, colorless, odorless, and chemically stable. For these reasons and others, PEG has been selected as the preferred polymer for attachment, but it has been employed solely for purposes of illustration and not limitation. Similar products may be obtained with other water-soluble polymers, including without limitation: polyvinyl alcohol, other poly(alkylene oxides) such as poly(propylene glycol) and the like, poly (oxyethylated polyols) such as poly(oxyethylated glycerol) and the like, carboxymethylcellulose, dextran, polyvinyl alcohol, polyvinyl purrolidone, poly-1,3-dioxolane, poly-1, 3,6-trioxane, ethylene/maleic anhydride, and polyaminoacids. One skilled in the art will be able to select the desired polymer based on the desired dosage, circulation time, resistance to proteolysis, and other considerations.

In particular, a wide variety of PEG derivatives are both available and suitable for use in the preparation of PEG-conjugates. For example, NOF Corp.'s PEG reagents sold under the trademark SUNBRIGHT® Series provides numerous PEG derivatives, including methoxypolyethylene glycols and activated PEG derivatives such as methoxy-PEG amines, maleimides, N-hydroxysuccinimide esters, and carboxylic acids, for coupling by various methods to the N-terminal, C-terminal or any internal amino acid of the AARS polypeptide. Nektar Therapeutics' Advanced PEGylation technology also offers diverse PEG-coupling technologies to potentially improve the safety and efficacy of an AARS polypeptide based therapeutic.

A search of patents, published patent applications, and related publications will also provide those skilled in the art reading this disclosure with significant possible PEG-coupling technologies and PEG-derivatives. For example, U.S. Pat. Nos. 6,436,386; 5,932,462; 5,900,461; 5,824,784; and 4,904,584; the contents of which are incorporated by reference in their entirety, describe such technologies and derivatives, and methods for their manufacture.

In addition, the present invention provides a fusion protein comprising the polypeptide and a heterologous fusion partner.

The fusion polypeptide refers to the polypeptide of the present invention which is covalently bonded to at least one heterologous sequence (fusion partner) directly or indirectly via an amino acid linker. In a fusion protein, the constituent polypeptides are generally fused to each other by linking the C-terminus to the N-terminus; however, the fusion polypeptide may be constructed by linking C-terminus to C-terminus, N-terminus to N-terminus, or N-terminus to C-terminus. The constituent polypeptides may be in an arbitrary order in the fusion protein.

Fusion partners are essentially (basically, principally) designed and included for any desirable purpose. However, they do not have harmful influences on the desirable activity of the polypeptide. In an embodiment, for example, the fusion partner includes a sequence (expression enhancer) for assisting the expression of the protein at higher yield than the natural recombinant protein. Other fusion partners may be selected so as to increase the solubility of the polypeptide or to enable the polypeptide to be targeted to desired intracellular compartments. Still further, fusion partners include affinity tags, which facilitate purification of the polypeptide.

As a preferable example, the fusion partner may be an antibody or a fragment thereof. In addition, for example, the fragment may be selected from the group consisting of Fc, diabodies, Fab, Fab', F(ab)2, F(ab')2, Fv, and scFv.

Examples of fusion proteins that improve pharmacokinetic properties ("PK modifiers") include without limitation, fusions to human albumin, antibody Fe domains, poly Glu or poly Asp sequences, and transferrin. Additionally, fusion with conformationally disordered polypeptide sequences composed of the amino acids Pro, Ala, and Ser ('PASylation') or hydroxyethyl starch (sold under the trademark HESYLATION®) provides a simple way to increase the hydrodynamic volume of the AARS polypeptide. This additional extension adopts a bulky random structure, which significantly increases the size of the resulting fusion protein. By this means the typically rapid clearance of smaller AARS polypeptides via kidney filtration is retarded by several orders of magnitude. Additional use of Ig G fusion proteins has also been shown to enable some fusion protein proteins to penetrate the blood brain barrier.

Examples of fusion proteins that improve penetration across cellular membranes include fusions to membrane translocating sequences. In this context, the term "membrane translocating sequences" refers to naturally occurring and synthetic amino acid sequences that are capable of membrane translocation across a cellular membrane. Representative membrane translocating sequences include those based on the naturally occurring membrane translocating sequences derived from the Tat protein, and homeotic transcription protein Antennapedia, as well as synthetic membrane translocating sequences based in whole or part on poly arginine and lysine resides. Representative membrane translocating sequences include for example those disclosed in the following patents: U.S. Pat. Nos. 5,652,122; 5,670,617; 5,674,980; 5,747,641; 5,804,604; 6,316,003; 7,585,834; 7,312,244; 7,279,502; 7,229,961; U.S. Pat. Nos. 7,169,814; 7,453,011; 7,235,695; 6,982,351; 6,605,115; 7,306,784; 7,306,783; 6,589,503; 6,348,185; 6,881,825; 7,431,915; WO0074701A2; WO2007111993A2; WO2007106554A2; WO02069930A1; WO03049772A2; WO03106491A2; and WO2008063113A1.

Fusion polypeptides may generally be prepared using standard techniques. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides. The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn, and Ser residues. Other near neutral amino acids, such as Thr and Ala may also be used in the linker sequence. Amino acid sequences which may be usefully employed as linkers include those disclosed in Maratea et al., Gene 40:39 46 (1985); Murphy et al., Proc. Natl. Acad. Sci. USA 83:8258 8262 (1986); U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

In general, polypeptides and fusion polypeptides (as well as polynucleotides coding therefor) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure, and most preferably at least about 99% pure. A polynucleotide is considered to be isolated if, for example, it is cloned into a vector that is not a part of the natural environment.

In addition, the present invention provides a dimeric or multimeric complex comprising at least one of the polypeptide.

In an embodiment, the polypeptide of the present invention may be part of a dimer. Dimers may include, for example, homodimers between two identical GRS polypeptides, heterodimers between two different GRS polypeptides (e.g., a full-length GRS polypeptide and a truncated GRS polypeptide; or two different truncated GRS polypeptides), and/or heterodimers between a GRS polypeptide and a heterologous polypeptide. Certain heterodimers, such as those between a GRS polypeptide and a heterologous polypeptide, may be bi-functional.

In addition, the polypeptide of the invention may be part of a multi-unit complex. A multi-unit complex of the present invention can include, for example, at least 3, 4, or 5 or more monomers. The monomers and/or multi-unit complexes of the present invention may be soluble and may be isolated or purified to homogeneity. Monomer units of a multi-unit complex may be different, homologous, substantially homologous, or identical to one another.

Covalently linked monomers can be linked directly (by bonds) or indirectly (e.g., via a linker). For directly linking the polypeptide herein, it may be beneficial to modify the polypeptides to enhance dimerization. For example, one or more amino acid residues of a GRS polypeptide may be modified by the addition or substation by one or more cysteines. Methods for creating amino acid substitutions, such as cysteine substitutions, or other modifications to facilitate linking, are well known to those skilled in the art.

In addition, the present invention provides an isolated polynucleotide encoding the polypeptide, and a composition comprising the polynucleotide.

As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of the present invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be recognized by those skilled in the art, polynucleotides may be single-stranded (coding or antisense sequences) or double-stranded, and may be DNA (genomic, cDNA or synthetic) or RNA molecules. Additional coding or non-coding sequences may be present within a polynucleotide of the present invention, and a polynucleotide may, but need not, be linked to other molecules and/or support materials.

Polynucleotides may comprise a native sequence or may comprise a variant, or a biological functional equivalent of such a sequence. Polynucleotide variants may contain one or more substitutions, additions, deletions and/or insertions, as further described below, preferably such that the desired non-canonical activity of the encoded polypeptide is not substantially diminished relative to the unmodified polypeptide. The effect on the activity of the encoded polypeptide may generally be assessed as described herein.

In a further embodiment, the present invention provides isolated polynucleotides comprising various lengths of contiguous stretches of sequence identical to or complementary to a glycyl-tRNA synthetase, wherein the isolated polynucleotides encode polypeptide fragments described herein.

So long as the polynucleotides provided by the present invention encode the isolated polypeptides or variants thereof according to the present invention, no particular limitations are imparted to concrete sequences thereof, but any combination of base sequences (nucleic acid sequences) may be permitted. For example, the peptide (GRS-DP-B, GRS 531-538) of SEQ ID NO: 2 may be expressed from a polynucleotide containing the base sequence of SEQ ID NO: 8, but with no limitations thereto. In another embodiment, the peptide (GRS-DP-A linear, GRS 531-555) of SEQ ID NO: 3 may be expressed from a polynucleotide containing the base sequence of SEQ ID NO: 9, but with no limitations thereto. In another embodiment, the peptide (GRS-DP, GRS 531-600) of SEQ ID NO: 4 may be expressed from a polynucleotide containing the base sequence of SEQ ID NO: 10, but with no limitations thereto. In another embodiment, the peptide (GRS-DP-A cyclic) of SEQ ID NO: 7 may be expressed from a polynucleotide containing the base sequence of SEQ ID NO: 11, but with no limitations thereto.

In another embodiment, the present invention contemplates a polynucleotide that can hybridize with the polynucleotide sequence provided herein, or a fragment thereof, or a complementary sequence thereof under moderately stringent conditions. Hybridization technique is known in the molecular biology field. By way of example, moderately stringent conditions suitable to test the hybridization of the polynucleotides of the present invention with other polynucleotides include prewashing in a solution of 5×SSC, 0.5% SDS, 1.0 mM EDTA (pH 8.0); hybridizing at 50° C. to 65° C., 5×SSC, overnight; followed by washing twice at 65° C. for 20 minutes with each of 2×, 0.5× and 0.2×SSC containing 0.1% SDS.

The polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed with the total length preferably being limited by the ease of preparation and use in the intended recombinant DNA protocol.

It will be appreciated by those of ordinary skill in the art that, as a result of the degeneracy of the genetic code, there are many nucleotide sequences that encode a polypeptide as described herein. Some of these polynucleotides contain minimal homology to the nucleotide sequence of any native gene. Nonetheless, polynucleotides (e.g., polynucleotides optimized for codon selection of humans and/or primates) that vary due to differences in codon usage are specifically contemplated by the present invention.

Furthermore, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides and fusions thereof may be prepared, manipulated and/or expressed using any of a variety of techniques known and available in the art. For example, polynucleotide sequences which encode polypeptides of the invention, or fusion proteins or functional equivalents thereof, may be used in recombinant DNA molecules to direct expression of the polypeptide of the invention in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties (e.g., a half-life which is longer than that of a transcript generated from the naturally occurring sequence).

Moreover, the polynucleotide sequences of the present invention can be engineered using methods generally known in the art in order to alter polypeptide encoding sequences for a variety of reasons (including but not limited to, alterations which modify the cloning, processing, expression and/or activity of the gene product).

In addition, the present invention provides an expression vector comprising the polynucleotide and a host cell comprising the expression vector.

In order to express a desired polypeptide, a nucleotide sequence encoding the polypeptide or a functional equivalent thereof may be inserted into appropriate expression vector (i.e., a vector which contains the necessary elements for the transcription and translation of the inserted coding sequence). Methods which are well known to those skilled in the art may be used to construct expression vectors containing sequences encoding a polypeptide of interest and appropriate transcriptional and translational regulatory elements. These methods include in vitro recombinant DNA techniques, synthetic techniques, and in vivo genetic recombination.

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems, including viral-based expression systems.

The "control elements" or "regulatory sequences" present in an expression vector are those non-translated regions of the vector (enhancers, promoters, 5' and 3' untranslated regions) which interact with host cellular proteins to carry out transcription and translation. Such elements may vary in their strength and specificity. Depending on the vector system and host utilized, any number of suitable transcription and translation elements, including constitutive and inducible promoters, may be used.

For example, when cloning in bacterial systems, inducible promoters such as the hybrid lacZ promoter of the PBLUE-SCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, vectors which direct high level expression of fusion proteins that are readily purified may be used. Such vectors include, but are not limited to, the following: multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced); pIN vectors (Van Heeke & Schuster, J.Biol.Chem.264:5503 5509(1989); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor Xa protease cleavage sites so that the cloned polypeptide of interest can be released from the GST moiety at will.

In the yeast *Saccharomyces cerevisiae*, a number of vectors containing constitutive or inducible promoters (such as alpha factor, alcohol oxidase, and PGH) may be used.

In cases where plant expression vectors are used, the expression of sequences encoding polypeptides may be driven by any of a number of promoters. For example, viral promoters (e.g., the 35S and 19S promoters of CaMV) may be used alone or in combination with the omega leader sequence from TMV (Takamatsu, EMBO J. 6:307-311 (1987)). Alternatively, plant promoters such as the small subunit of RUBISCO or heat shock promoters may be used. These constructs can be introduced into plant cells by direct DNA transformation or pathogen-mediated transfection. Such techniques are known in the art.

An insect system may also be used to express a polypeptide of interest. For example, in one such system, AcNPV (*Autographa californica* nuclear polyhedrosis virus) is used as a vector to express foreign genes in *Spodoptera frugiperda* cells or in *Trichoplusia* larvae. The sequences encoding the polypeptide may be cloned into a non-essential region of the virus, such as the polyhedrin gene, etc., and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* larvae in which the polypeptide of interest may be expressed.

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan and Shenk Proc. Natl. Acad. Sci. U.S.A. 81:3655-3659 (1984)). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used.

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation. Post-translational processing which cleaves a "prepro" form of the protein may also be used to facilitate correct insertion, folding and/or function. Different host cells (such as yeast, CHO, HeLa, MDCK, HEK293, and W138, which have or even lack specific cellular machinery and characteristic mechanisms for such post-translational activities) may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector.

Following the introduction of the vector, cells may be allowed to grow for about 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

A number of selection systems may be used to recover transformed or transduced cell lines. These include, but are not limited to, the herpes simplex virus thymidine kinase (Wigler et al., Cell 11:223-232 (1977)) and adenine phosphoribosyltransferase (Lowy et al., Cell 22:817-823 (1990)) genes which can be employed in tk- or aprt-cells, respectively.

Also, antimetabolite, antibiotic or herbicide resistance can be used as the basis for selection; for example, dhfr which confers resistance to methotrexate (Wigler et al., Proc.Natl.Acad.Sci.U.S.A. 77:3567~70(1980)); npt, which confers resistance to the aminoglycosides, neomycin and G-418 (Colbert-Garapin et al., J.Mol.Biol. 150:1~14(1981)); and als or pat, which confer resistance to chlorsulfuron and phosphinotricin acetyltransferase, respectively. Additional selectable genes have been described, for example, trpB, which allows cells to utilize indole in place of tryptophan, or hisD, which allows cells to utilize histinol in place of histidine (Hartman and Mulligan, Proc. Natl. Acad. Sci. U.S.A. 85:8047-51 (1988)). The use of visible markers has gained popularity with such markers as green fluorescent protein (GFP) and other fluorescent proteins (e.g., RFP, YFP), anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., Methods Mol. Biol. 55:121-131 (1995)).

Various protocols for detecting and measuring the expression of polynucleotide-encoded products, using any one of polyclonal or monoclonal antibodies specific for the product, are known in the art. Examples include ELISA (enzyme-linked immunosorbent assay), RIA (radioimmunoassay), FACS (fluorescence activated cell sorting), and so on. These and other assays are well known in the art. A variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase (e.g., T7, T3, or SP6) and labeled nucleotides. These procedures may be conducted using a variety of commercially available kits. Suitable reporter molecules or labels, which may be used include radionuclides, enzymes, fluorescers, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by the recombinant cell may be secreted or contained intracellularly depending on the sequence and/or the vector used.

As will be understood by those of skill in the art, expression vectors carrying polynucleotides of the present invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification and/or detection of soluble proteins.

In addition to recombinant production methods, polypeptides of the invention and fragments thereof may be produced by direct peptide synthesis using solid-phase techniques. Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the desired molecule.

According to another aspect of the invention, polynucleotides encoding polypeptides of the invention may be delivered to a subject in vivo, e.g., using gene therapy techniques. Gene therapy refers generally to the transfer of heterologous nucleic acids to the certain cells, target cells, of a mammal, particularly a human, with a disorder or conditions for which such therapy is sought. The nucleic acid is introduced into the selected target cells in a manner such that the heterologous DNA is expressed and a therapeutic product encoded thereby is produced.

Various viral vectors that can be utilized for gene therapy as disclosed herein include adenovirus, herpes virus, vaccinia, AAV (adeno-associated virus), or, preferably, an RNA virus such as a retrovirus. Preferably, the retroviral vector is a derivative of a murine or avian retrovirus, or is a lentiviral vector. The preferred retroviral vector is a lentiviral vector. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of additional retroviral vectors can incorporate multiple genes. All of these vectors can transfer or incorporate a gene for a selectable marker so that transduced cells can be identified and generated. By inserting a zinc finger derived-DNA binding polypeptide sequence of interest into the viral vector, along with another gene that encodes the ligand for a receptor on a specific target cell, for example, the vector may be made target specific.

Retroviral vectors can be made target specific by inserting, for example, a polynucleotide encoding a polypeptide. Illustrative targeting may be accomplished by using an antibody to target the retroviral vector. Those of skill in the art can readily ascertain without undue experimentation, specific polynucleotide sequences which can be inserted into the retroviral genome to allow target specific delivery of the retroviral vector containing the zinc finger-nucleotide binding protein polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsulation. Helper cell lines which have deletions of the packaging signal include but are not limited to PSI.2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line (e.g., NIH 3T3 cells) to produce large quantities of chimeric retroviral virions.

"Non-viral" delivery techniques for gene therapy can also be used including, for example, DNA-ligand complexes, adenovirus-ligand-DNA complexes, direct injection of DNA, CaPO$_4$ precipitation, gene gun techniques, electroporation, liposomes, lipofection, and the like. Any of these methods are widely available to one skilled in the art and would be suitable for use in the present invention. Other suitable methods are available to one skilled in the art, and it is to be understood that the present invention can be accomplished using any of the available methods of transfection. Lipofection can be accomplished by encapsulating an isolated DNA molecule within a liposomal particle and contacting the liposomal particle with the cell membrane of the target cell. Liposomes are self-assembling, colloidal particles in which a lipid bilayer, composed of amphiphilic molecules such as phosphatidyl serine or phosphatidyl choline, encapsulates a portion of the surrounding media such that the lipid bilayer surrounds a hydrophilic interior. Unilammellar or multilammellar liposomes can be constructed such that the interior contains a desired chemical, drug, or, as in the instant invention, an isolated DNA molecule.

In addition, the present invention provides a composition (hereinafter referred to as "GRS composition") comprising a physiologically acceptable carrier and at least one selected from the group consisting of:

(i) the polypeptide of the present invention,
    (ii) a fusion protein comprising the polypeptide of (i) and a heterologous fusion partner,
    (iii) a dimeric or multimeric complex comprising at least one polypeptide of (i),
    (iv) a polynucleotide encoding (i) to (iii),
    (v) an expression vector comprising (iv), and
    (vi) a host cell comprising (v).

The composition (e.g., polypeptide, polynucleotide, etc.) of the present invention may be formulated in pharmaceutically-acceptable or physiologically-acceptable solutions for administration to a cell or an animal, either alone, or in combination with one or more other modalities of therapy. It will also be understood that, if desired, the composition of the invention may be administered in combination with other agents as well (e.g., other proteins or polypeptides or various pharmaceutically active agents). There is no limit to other components that may also be included in the compositions, provided that the additional agents do not adversely affect the modulatory or other effects desired to be achieved.

In the pharmaceutical composition of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, subcutaneous, and intramuscular administration and formulation.

In certain applications, the pharmaceutical composition disclosed herein may be delivered via oral administration to a subject. As such, the composition may be formulated with an inert diluent or with an assimilable edible carrier, or the composition may be enclosed in hard- or soft-shell gelatin capsules, or the composition may be compressed into tablets, or the composition may be incorporated directly with the food of the diet.

In certain circumstances it will be desirable to deliver the pharmaceutical composition disclosed herein parenterally, intravenously, intramuscularly, or intraperitoneally. For such administration routes, reference may be made to U.S. Pat. Nos. 5,543,158; 5,641,515 and 5,399,363. Solutions of the active compounds (as free base or pharmacologically acceptable salts) may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (refer to U.S. Pat. No. 5,466,468). In all cases the form should be sterile and should be fluid to the extent that easy syringeability exists. It should be stable under the conditions of manufacture and storage and should be preserved against the contaminating action of microorganisms, such as bacteria and fungi. The carrier may be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents (for example, sugars or sodium chloride). Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this context, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids (e.g., hydrochloric or phosphoric acids), or organic acids (e.g., acetic acid, oxalic acid, tartaric acid, mandelic acid, and the like). Salts formed with the free carboxyl groups can also be derived from inorganic bases (e.g., sodium, potassium, ammonium, calcium, or ferric hydroxides), and organic bases (e.g., isopropylamine, trimethylamine, histidine, procaine and the like). Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, the term "carrier" is indented to encompass any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the pharmaceutical composition may be delivered by intranasal sprays, inhalation, and/or other aerosol delivery vehicles. Methods for delivering genes, polynucleotides, and peptide compositions directly to the lungs via nasal aerosol sprays have been described, for example, in U.S. Pat. Nos. 5,756,353 and 5,804,212. Likewise, the delivery of drugs using intranasal microparticle resins (Takenaga et al., 1998) and lysophosphatidyl-glycerol compounds (U.S. Pat. No. 5,725,871) are also well known in the pharmaceutical arts. Likewise, for transmucosal drug delivery in the form of a polytetrafluoroetheylene support matrix, reference can be made to U.S. Pat. No. 5,780,045.

In certain embodiments, the delivery may be carried out by use of liposomes, nanocapsules, microparticles, microspheres, lipid particles, vesicles, and the like, for the introduction of the composition of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

In addition, the pharmaceutical composition of the present invention may be formulated using a method known in the art to provide immediate, sustained, or delayed release of the active ingredient after being administered to a mammalian animal. The pharmaceutical compositions formulated by the above methods may be administered in an effective amount via various routes including oral, transdermal, hypodermic, vein, or muscle, as described above. Here, "effective amount" means an amount of substance which makes it possible to trace a diagnostic or therapeutic effect when the pharmaceutical composition is medicated to a patient. The pharmaceutical composition comprising the polypeptide of the present invention may contain the active ingredient in different amounts according to the severity of the disease and may be administered at a single dose of 0.1 μg to 10,000 mg and preferably 1 mg to 5,000 mg for an adult repeatedly a day. However, the dosage amount of the pharmaceutical composition according to the present invention may be properly selected in consideration of administration routes used, age, sex, body weight, medical condition and/or other personal differences of the subject. These techniques are well known to those skilled in the art.

In another aspect thereof, the present invention provides a method of using the composition (e.g., polynucleotide, polypeptide, or the like) of the present invention in a cell, a tissue, or a subject so as to accomplish a desirable cellular effect and/or therapeutic effect. The cells or tissues that may be treated or modulated by the present invention are preferably mammalian cells or tissues, or more preferably human cells or tissues. Such cells or tissues can be of a healthy state or of a diseased state.

In certain embodiments, a method is provided for modulating therapeutically relevant cellular activities including, but not limited to, cellular metabolism, cell differentiation, cell proliferation, cellular uptake, cell secretion, cell death, cell mobilization, cell migration, cell signaling, modulation of cytokine production and/or secretion, gene transcription, mRNA translation, cell impedance, and the like, the method comprising contacting a cell with a GRS composition as described herein. In another particular embodiment, the cellular activity modulated by the present invention may include, for example, AKT-mediated cell signaling, ERK1/2-mediated cell signaling, GPCR-mediated cell signaling, endothelial cell tube formation, and cell binding. In another particular embodiment, the cellular activity may include, for example, modulation of CD71 and/or CD80. In another particular embodiment, the cellular activity may include, for example, modulation of cytokine production and/or secretion, and the cytokine may be selected from the group consisting of TNF-α, IL1-β, IL-6, IL-8, IL-10, IL-12p40, MIP1-α, MIP-1β, GRO-α, MCP-1, and IL-1ra. In another particular embodiment, the cellular activity may include, for example, metabolic regulation through cellular modulation of glucose, glucagon, glycerol, and/or free fatty acid. In another particular embodiment, the cellular activity may include, for example, modulation of neurogenesis or neuroprotection. Therefore, the GRS composition may be employed in treating essentially any cell or tissue or subject that would benefit from modulation of one or more such activities.

The GRS composition may also be used in any of a number of therapeutic contexts including, for example, those relating to the treatment or prevention of neoplastic diseases, immune system diseases or conditions (e.g., autoimmune diseases and inflammation), infectious diseases, metabolic diseases, neuronal/neurological diseases, muscular/cardiovascular diseases, diseases associated with aberrant hematopoiesis, diseases associated with aberrant myogenesis, diseases associated with aberrant neurogenesis, diseases associated with aberrant adipogenesis, diseases associated with aberrant osteogenesis, diseases associated with aberrant angiogenesis, diseases associated with aberrant cell survival, and others.

For example, in certain illustrative embodiments, the GRS compositions of the present invention may be used to modulate angiogenesis, e.g., via modulation of endothelial cell proliferation and/or signaling. Endothelial cell proliferation and/or signaling may be monitored using an appropriate cell line (e.g., HMVEC-L (human microvascular endothelial lung cells) and HUVEC (human umbilical vein endothelial cells)), and using an appropriate assay (e.g., endothelial cell migration assays, endothelial cell proliferation assays, tube-forming assays, matrigel plug assays, etc.), many of which are known in the art.

Accordingly, the present invention provides a pharmaceutical composition comprising the polypeptide or polynucleotide of the present invention as an active ingredient for prevention or treatment of a neoplastic disease.

As proven in the Example section herein, polypeptide fragments of certain lengths (isolated GRS polypeptides and variants thereof) containing the motif revealed in the present invention exhibit excellent cell apoptotic activity, particularly, excellent inhibitory activity against aberrant cell growth. This effect is superior to those at the full-length GRS protein level or at the domain level. Therefore, the present invention provides a therapeutic use of the polypeptide or polynucleotide of the present invention in a neoplastic disease.

The neoplastic disease may be selected from the group consisting of colon cancer, cardiac tumors, pancreatic cancer, melanoma, retinoblastoma, glioblastoma, lung cancer, intestinal cancer, testicular cancer, stomach cancer, neuroblastoma, osteosarcoma, chondrosarcoma, adenoma, breast cancer, prostate cancer, Kaposi's sarcoma, ovarian cancer, leukemia, myelodysplastic syndrome, polycythemia vera, lymphoma, multiple myeloma, renal cell carcinoma, solid tumor, and angiogenesis-related diseases.

Therefore, in related embodiments, the composition of the invention may be applied to the treatment of any cell or tissue or subject that would essentially benefit from modulation of angiogenesis. For example, in some embodiments, a cell or tissue or subject experiencing or susceptible to angiogenesis (e.g., an excessive angiogenic condition) may be contacted with a suitable composition of the invention to inhibit an angiogenic condition. In other embodiments, a cell or tissue experiencing or susceptible to insufficient angiogenesis (e.g., an angiostatic condition) may be contacted with an appropriate composition of the invention in order to interfere with angiostatic activity and/or promote angiogenesis.

The angiogenesis-related disease, that is, inappropriate angiogenic condition, may be selected from the group consisting of age-related macular degeneration (AMD), cancer (both solid and hematologic), developmental abnormalities (organogenesis), diabetic blindness, endometriosis, ocular neovascularization, skin discolorations (e.g. hemangioma, nevus flammeus, nevus simplex, and the like), diabetic retinopathy, retinopathy of prematurity, neovascular glaucoma, erythrosis, proliferative retinopathy, psoriasis, hemophilic arthropathy, capillary proliferation in atheromatous atherosclerotic plaques, keloid, wound granulation, angiostenosis, rheumatoid arthritis, osteoarthritis, autoimmune diseases, Crohn's disease, restenosis, atheromatous arteriosclerosis, cat scratch disease, ulcers, glomerulonephritis, diabetic nephropathy, malignant nephrosclerosis, thrombotic microangiopathy, glomerulopathy, and inflammation, with no limitations thereto.

In other embodiments, the ARS compositions of the invention may be used to modulate cellular proliferation and/or survival and, accordingly, for treating or preventing diseases, disorders or conditions characterized by abnormalities in cellular proliferation and/or survival. For example, in certain embodiments, the ARS compositions may be used to modulate apoptosis and/or to treat diseases or conditions associated with abnormal apoptosis. Apoptosis is the term used to describe the cell signaling cascade known as programmed cell death. Various therapeutic indications exist for molecules that induce apoptosis (e.g. cancer), as well as those that inhibit apoptosis (i.e. stroke, myocardial infarction, sepsis, etc.). Apoptosis can be monitored by any of a number of available techniques known and available in the art including, for example, assays that measure fragmentation of DNA, alterations in membrane asymmetry, activation of apoptotic caspases and/or release of cytochrome C and AIF.

Illustrative diseases associated with increased cell survival or the inhibition of apoptosis include, but are not limited to, cancers (such as follicular lymphomas, carcinomas, and hormone-dependent tumors, including colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma, and ovarian cancer); autoimmune disorders (such as, multiple sclerosis, Sjogren's syndrome, Graves' disease, Hashimoto's thyroiditis, autoimmune diabetes, biliary cirrhosis, Behcet's disease, Crohn's disease, polymyositis, systemic lupus erythematosus and immune-related glomerulonephritis, autoimmune gastritis, autoimmune thrombocytopenic purpura, and rheumatoid arthritis) and viral infections (such as herpes viruses, pox viruses and adenoviruses), inflammation, graft vs. host disease (acute and/or chronic), acute graft rejection, and chronic graft rejection.

Further illustrative diseases or conditions associated with increased cell survival include, but are not limited to, progression and/or metastases of malignancies and related disorders such as leukemia (including acute leukemias (for example, acute lymphocytic leukemia, acute myelocytic leukemia, including myeloblastic, promyelocytic, myelomonocytic, monocytic, and erythroleukemia)) and chronic leukemias (for example, chronic myelocytic (granulocytic) leukemia and chronic lymphocytic leukemia), myelodysplastic syndrome polycythemia vera, lymphomas (for example, Hodgkin's disease and non-Hodgkin's disease), multiple myeloma, Waldenstrom's macroglobulinemia, heavy chain diseases, and solid tumors. The solid tumors may include, but is not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

The composition of the invention may also be useful as an immunomodulator for treating anti- or pro-inflammatory indications by modulating the cells that mediate, either directly or indirectly, autoimmune and/or inflammatory disease, conditions and disorders. The utility of the composition of the invention as an immunomodulator can be monitored using any of a number of known techniques in the art including, for example, migration assays (e.g., using leukocytes, lymphocytes, monocytes), cell viability assays (e.g., using B-cells, T-cells, monocytes, NK cells), or the like.

Examples of immune system diseases, disorders or conditions that may be treated according to the present invention include, but are not limited to, primary immunodeficiency, immune-mediated thrombocytopenia, Kawasaki syndrome, bone marrow transplant (for example, bone marrow transplant in adults or children), chronic B cell lymphocytic leukemia, human immunodeficiency virus (HIV) infection (for example, adult or pediatric HIV infection), chronic inflammatory demyelinating polyneuropathy, posttransfusion purpura, and the like.

Additionally, further diseases, disorders and conditions that may be treated according to the present invention include Guillain-Barre syndrome, anemia (for example, anemia associated with parvovirus B19), patients with stable multiple myeloma who are at high risk for infection (for example, recurrent infection), autoimmune hemolytic anemia (for example, warm-type autoimmune hemolytic anemia), thrombocytopenia (for example, neonatal thrombocytopenia), and immune-mediated neutropenia), transplantation (for example, cytomegalovirus (CMV)-negative recipients of CMV-positive organs), hypogammaglobulinemia (for example, hypogammaglobulinemic neonates with risk factor for infection or morbidity), epilepsy (for example, intractable epilepsy), systemic vasculitic syndromes, myasthenia gravis (for example, decompensation in myasthenia gravis), dermatomyositis, and polymyositis.

Further autoimmune diseases, disorders and conditions include but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (for example, IgA nephropathy), multiple sclerosis, neuritis, uveitis ophthalmia, polyendocrinopathies, purpura (for example, Henloch-Scoenlein purpura), Reiter's disease, stiff-man syndrome, autoimmune pulmonary inflammation, Guillain-Barre Syndrome, insulin dependent diabetes mellitus, and autoimmune inflammatory eye disease.

Additional autoimmune diseases, disorders or conditions include, but are not limited to, autoimmune thyroiditis; hypothyroidism, including Hashimoto's thyroiditis and thyroiditis characterized, for example, by cell-mediated and humoral thyroid cytotoxicity; SLE (which is often characterized, for example, by circulating and locally generated immune complexes); Goodpasture's syndrome (which is often characterized, for example, by anti-basement membrane antibodies); pemphigus (which is often characterized, for example, by epidermal acantholytic antibodies); receptor autoimmunities such as, for example, Graves' disease (which is often characterized, for example, by antibodies to a thyroid stimulating hormone receptor; myasthenia gravis, which is often characterized, for example, by acetylcholine receptor antibodies); insulin resistance (which is often characterized, for example, by insulin receptor antibodies); autoimmune hemolytic anemia (which is often characterized, for example, by phagocytosis of antibody-sensitized red blood cells); and autoimmune thrombocytopenic purpura (which is often characterized, for example, by phagocytosis of antibody-sensitized platelets).

Additional autoimmune diseases, disorders or conditions include, but are not limited to, rheumatoid arthritis (which is often characterized, for example, by immune complexes in joints); scleroderma with anti-collagen antibodies (which is often characterized, for example, by nucleolar and other nuclear antibodies); mixed connective tissue disease, (which is often characterized, for example, by antibodies to extractable nuclear antigens, for example, ribonucleoprotein); polymyositis/dermatomyositis (which is often characterized, for example, by nonhistone anti-nuclear antibodies); pernicious anemia (which is often characterized, for example, by antiparietal cell, antimicrosome, and anti-intrinsic factor antibodies); idiopathic Addison's disease (which is often characterized, for example, by humoral and cell-mediated adrenal cytotoxicity); infertility (which is often characterized, for example, by anti-spennatozoal antibodies); glomerulonephritis (which is often characterized, for example, by glomerular basement membrane antibodies or immune complexes); by primary glomerulonephritis, by IgA nephropathy; bullous pemphigoid (which is often characterized, for example, by IgG and complement in the basement membrane); Sjogren's syndrome (which is often characterized, for example, by multiple tissue antibodies and/or the specific nonhistone antinuclear antibody (SS-B)); diabetes mellitus (which is often characterized, for example, by cell-mediated and humoral islet cell antibodies); and adrenergic drug resistance, including adrenergic drug resistance with asthma or cystic fibrosis (which is often characterized, for example, by beta-adrenergic receptor antibodies).

Still further autoimmune diseases, disorders or conditions include, but are not limited to chronic active hepatitis (which is often characterized, for example by smooth muscle antibodies); primary biliary cirrhosis (which is often characterized, for example, by anti-mitochondrial antibodies); other endocrine gland failure (which is characterized, for example, by specific tissue antibodies in some cases); vitiligo (which is often characterized, for example, by anti-melanocyte antibodies); vasculitis (which is often characterized, for example, by immunoglobulin and complement in vessel walls and/or low serum complement); post-myocardial infarction conditions (which are often characterized, for example, by anti-myocardial antibodies); cardiotomy syndrome (which is often characterized, for example, by anti-myocardial antibodies); urticaria (which is often characterized, for example, by IgG and IgM antibodies to IgE); atopic dermatitis (which is often characterized, for example, by IgG and IgM antibodies to IgE); asthma (which is often characterized, for example, by IgG and IgM antibodies to IgE); inflammatory myopathies; and other inflammatory, granulomatous, degenerative, and atrophic disorders.

Furthermore, additional embodiments relate to the use of the compositions of the invention in the treatment of metabolic disorders such as adrenoleukodystrophy, Krabbe's disease (globoid cell leukodystrophy), metachromatic leukodystrophy, Alexander's disease, Canavan's disease (spongiform leukodystrophy), Pelizaeus-Merzbacher disease, Cockayne's syndrome, Hurler's disease, Lowe's syndrome, Leigh's disease, Wilson's disease, Hallervorden-Spatz disease, Tay-Sachs disease, etc. The utility of the compositions of the invention in modulating metabolic processes may be monitored using any of a variety of techniques known and available in the art including, for example, assays which measure adipocyte lipogenesis or adipocyte lipolysis.

In other particular embodiments, the GRS composition of the present invention may be used to modulate cellular signaling, for example, via kinase pathways (e.g., Akt, Erk1/2, etc.). Cell signaling may be monitored using any of a number of well-known assays. For example, the induction of general cell signaling events can be monitored through altered phosphorylation patterns of a variety of target proteins. Detection of cell signaling activities in response to treatment of cells with HRS polypeptides therefore serves as an indicator of distinct biological effects. Target proteins used for this assay may be selected so as to encompass key components of major cellular signaling cascades, thereby providing a broad picture of the cell signaling landscape and its therapeutic relevance. Generally, such assays involve cell treatment with HRS polypeptides followed by immunodetection with antibodies that specifically detect the phosphorylated (activated) forms of the target proteins.

Illustrative target proteins useful for monitoring therapeutically relevant cell signaling events may include, but are not limited to: p38 MAPK (mitogen-activated protein kinase; activated by cellular stress and inflammatory cytokines; involved in cell differentiation and apoptosis); SAPK/JNK (stress-activated protein kinase/Jun-amino-terminal kinase; activated by cellular stresses and inflammatory cytokines); Erk1/2, p44/42 MAPK (mitogen-activated protein kinase Erk1 and Erk2; activated by a wide variety of extracellular signals; involved in regulation of cell growth and differentiation); and Akt (activated by insulin and various growth or survival factors; involved in inhibition of apoptosis, regulation of glycogen synthesis, cell cycle regulation and cell growth). General phosphorylation of tyrosine residues may also be monitored as a general indicator of changes in cell signaling mediated by phosphorylation.

Of course, it will be recognized that other classes of proteins, such as cell adhesion molecules (e.g., cadherins, integrins, claudins, catenins, selectins, etc.) and/or ion channel proteins may also be assayed for monitoring cellular events or activities modulated by the compositions of the invention.

In still other aspects, the polynucleotides, polypeptides and/or other compositions of the present invention may be used in essentially any type of screening assay known and available in the art. For example, compositions of the invention (e.g., polypeptides and/or polynucleotides) may be used in conjunction with essentially any known screening methodology in order to identify agonists, antagonists, binding partners, competitive inhibitors), and cellular effectors that mediate or modulate, either directly or indirectly, the non-canonical activities of the compositions herein. For example, in a particular embodiment, a screening method is provided for identifying test compounds as inhibitors, or alternatively, potentiators, of an interaction between a composition of the invention and one or more of its binding partners, cellular effectors and/or cell types subject to modulation.

Accordingly, the present invention provides a screening method for identifying an anticancer agent, the method comprising the steps of:

(a) forming a reaction mixture containing (i) and (ii):
   (i) an ingredient selected from the group consisting of the polypeptide and the polynucleotide of the present invention,
   (ii) a test compound; and (b) determining an increase in an anti-cancer activity by the ingredient in the presence of the test compound, wherein a change in the anti-cancer activity in the presence of the test compound is determined compared to the anti-cancer activity in the absence of the test compound, thereby identifying an active test compound.

A statistically significant change (increase or decrease) in activity and or modulation in the presence of a test compound, compared to the absence thereof, accounts for a potential agonist (mimic or enhancer) or antagonist (inhibitor).

The screening methods provided herein may utilize test compounds from small molecule libraries generated by combinatorial chemistry. Libraries of chemical and/or biological mixtures, such as fungal, bacterial, or algal extracts, are known in the art and can be screened with any of the assays of the invention.

Libraries of compounds may be presented in solution or on beads, on chips, bacteria, spores (U.S. Pat. No. 5,223,409, 1993), plasmids, or on phage (U.S. Pat. No. 5,223,409, 1993). Embodiments of the present invention encompass the use of different libraries for the identification of small molecule modulators of one or more GRS protein fragments, their cellular binding partners, and/or their related non-canonical activities. Libraries useful for the purposes of the invention include, but are not limited to, (1) chemical libraries, (2) natural product libraries, and (3) combinatorial libraries comprised of random peptides, oligonucleotides, and/or organic molecules.

Chemical libraries consist of structural analogs of known compounds or compounds that are identified as "hits" or "leads" via natural product screening. Natural product libraries are derived from collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. Combinatorial libraries may be composed of large numbers of peptides, oligonucleotides or organic compounds as a mixture. They are relatively easy to prepare by traditional automated synthesis methods, PCR, cloning or proprietary synthetic methods. More specifically, a combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks. Such combinatorial chemistry and libraries produced therefrom are well known in the art.

The polypeptides (i.e., the isolated GRS polypeptides or GRS variants) provided herein exhibit a remarkable effect of specifically targeting cancer cells. In an embodiment of the present invention, the polypeptides of the present invention were identified to be specifically accumulated in tumor sites even when administered in a systemic manner. Therefore, the present invention provides a composition comprising the polypeptide of the present invention as an active ingredient for detection of cancer cells.

In the present invention, the cancer cells may be cadherin-6 (CDH6)-positive cancer cells, and concrete kinds of cancer cells are as described above.

The polypeptides of the present invention may be provided in a labeled state to facilitate identification, detection, and quantification of the binding of the polypeptides to tumor cells. In other words, the polypeptides may be linked (e.g., covalently bonded or crosslinked) with a detectable label. The detectable label may be chromogenic enzymes (e.g., peroxidase, alkaline phosphatase), radionuclides (e.g., $^{18}$F, $^{123}$I, $^{124}$I, $^{125}$I, $^{32}$P, $^{35}$S, $^{67}$Ga), chromophores, luminescent or fluorescers (e.g., FITC, RITC, fluorescent proteins (GFP (Green Fluorescent Protein); EGFP (Enhanced Green Fluorescent Protein), RFP (Red Fluorescent Protein); DsRed (Discosoma sp. red fluorescent protein); CFP (Cyan Fluorescent Protein), CGFP (Cyan Green Fluorescent Protein), YFP (Yellow Fluorescent Protein), Cy3, Cy5, and Cy7.5)), or magnetic resonance materials (e.g., gadolinium (Gd), super paramagnetic particles, or ultrasuper paramagnetic particles).

The detection method according to the label is widely known in the art, but can be performed, for example, by the following method. Immunofluorescence staining can be used with a fluorescent substance serving as a detectable label. For example, the peptide of the present invention labeled with a fluorescent substance can be reacted with a sample, and unbound or non-specific binding products can be removed, followed by observing the fluorescence of the peptide under a fluorescence microscope. In the case of using an enzyme as a detectable label, the absorbance can be measured by a color reaction of the substrate through an enzyme reaction. For a radioactive substance, the amount of emitted radiation can be measured. In addition, the detected result may be imaged using known imaging methods depending on the detection labels. Hence, the peptide of the present invention is available as an active ingredient of the composition for imaging cancer cells.

In addition, the present invention provides a method for detecting cancer cells, the method comprising the steps of:
(a) mixing the polypeptides with a biological sample;
(b) removing the polypeptides that remain unbound or are non-specifically bound; and
(c) determining whether and where the polypeptides are bound.

In this regard, the detection of the polypeptide in step (c) to determine whether and where the polypeptide is bound may be performed as described above or according to methods known in the art.

In the present invention, the term "sample" refers to a biological sample including blood and other liquid samples of biological origin, biopsy specimens, solid tissue samples such as tissue culture, or cells derived therefrom. The sample can be obtained from an animal, preferably a mammal. The sample may be pre-treated prior to use for detection. Such pre-treatment may include, for example, extraction, concentration, inactivation of interfering components, and addition of reagents.

Since the polypeptide of the present invention has an excellent effect of specifically binding to tumor cells, it can be used as an intelligent drug delivery vehicle for selectively delivering a drug to tumor cells. Accordingly, the present invention provides a composition comprising the polypeptide of the present invention as an active ingredient for cancer cell-specific drug delivery. In addition, the present invention provides a composition comprising the polypeptide of the present invention and an anticancer agent bound thereto as active ingredients for prevention and treatment of cancer.

More specifically, the peptide of the present invention contained in the drug delivery composition can deliver the conventional anti-tumor (cancer) agents associated therewith selectively to tumor cells only, thereby increasing the medicinal effects while remarkably reducing side effects on normal tissues.

So long as it is a well-known therapeutic agent for tumors, any anti-tumor agent may be bound to the peptide of the present invention Examples of the anti-tumor agent include paclitaxel, doxorubicin, vincristine, daunorubicin, vinblastine, actinomycin-D, docetaxel, etoposide, teniposide, bisantrene, homoharringtonine, Gleevec (STI-571), cisplain, 5-fluouracil, adriamycin, methotrexate, busulfan, chlorambucil, cyclophosphamide, melphalan, nitrogen mustard, nitrosourea, streptokinase, urokinase, alteplase, angiotensin II inhibitor, aldosterone receptor inhibitor, erythropoietin, NMDA (N-methyl-d-aspartate) receptor inhibitor, lovastatin, rapamycin, celebrex, ticlopin, marimastat, and trocade.

The binding between the agent and the peptide of the present invention may be made using a method known in the art, for example, covalent interaction, crosslinking, etc. In this regard, the peptide of the present invention may be chemically modified, if necessary, to the extent that the activity is not lost. The content of the peptide of the present invention in the composition of the present invention depends on kinds and amounts of the therapeutic agent. The polypeptide of the present invention may be linked to an anticancer agent via a covalent bond, especially a linker, but without limitations thereto.

The present invention provides a use of the polypeptide or the polynucleotide in preparing an agent for prevention and treatment of a neoplastic disease.

The present invention provides a method for prevention and treatment of a neoplastic disease, the method comprising a step of administering an effective amount of the composition comprising the polypeptide or the polynucleotide as an active ingredient to a subject in need thereof.

The present invention provides a use of the polypeptide in preparing an agent for detecting cancer cells, for imaging cancer cells, or for cancer cell-specific delivery of a drug.

The present invention provides a method for imaging cancer cells or for cancer cell-specific drug delivery, the method comprising a step of administering an effective amount of a composition comprising the peptide as an active ingredient to a subject in need thereof.

The present invention provides a use of the polypeptide and the anticancer agent bound thereto in preparing an agent for prevention and treatment of cancer.

The present invention provides a method for prevention and treatment of cancer, the method comprising a step of administering an effective amount of a composition comprising the polypeptide and an anticancer agent bound thereto as active ingredients to a subject in need thereof.

As used herein, the term "effective amount" refers to an amount showing alleviation, prevention, detection, or diagnostic effect on cancer when administered to a subject. The term "subject", as used herein, refers to an animal, preferably, a mammal including a human, or refers to a cell, tissue, or organ derived from an animal. Here, the subject may be a patient requiring the effect.

The term 'treatment' as used herein refers collectively to any action that alleviates cancer or cancer symptoms, and for example, may include curing, substantial preventing a disease or alleviating a cancer condition. The treatment may include any action to alleviate, treat, or prevent one cancer symptom or most of cancer symptoms, but with no limitations thereto.

Advantageous Effects

The polypeptides (polypeptides isolated from GRS, and variants thereof) disclosed herein contain the GRS cell apoptotic motif first found in the present invention and are provided as truncated forms having certain lengths. The polypeptides exhibit far higher activity and targeting ability than the full-length protein and the domain, finding high industrial availability in the medicinal industry.

Briefly, SN12C (CDH6 positive) cells were subcutaneously injected into BALB/c nude mice and then grown for 5 days to an average tumor size of 100 mm$^3$. On day 5 and 7, PBS or test materials were each injected at a dose of 20 µg into tumors (n=5 animals/group). Tumor volumes were calculated according to "maximum diameter×minimum diameter$^2$×0.52".

Figure 6A:
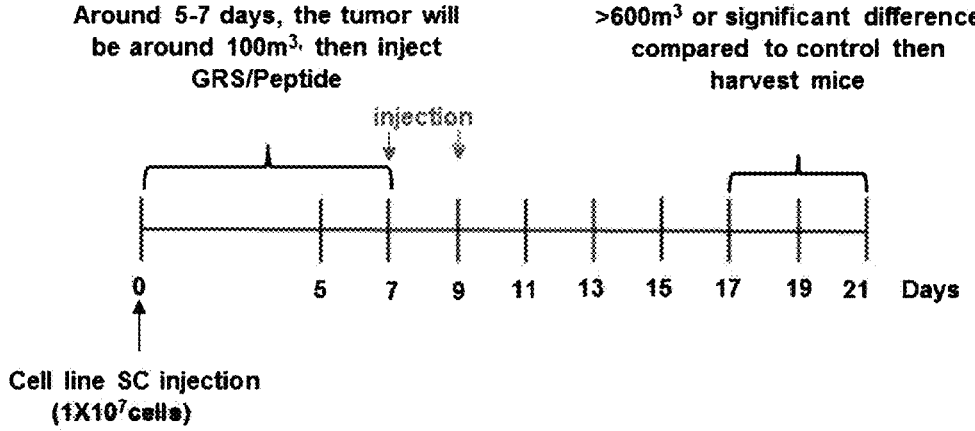
FIG. 6a is an experimental scheme for evaluating the ability of GRS, GRS-DP, and representative fragments derived therefrom (GRS-DP-B, or GRS-DP-A cyclic) to induce tumor regression in vivo by intra-tumor injection.
Figure 6B:
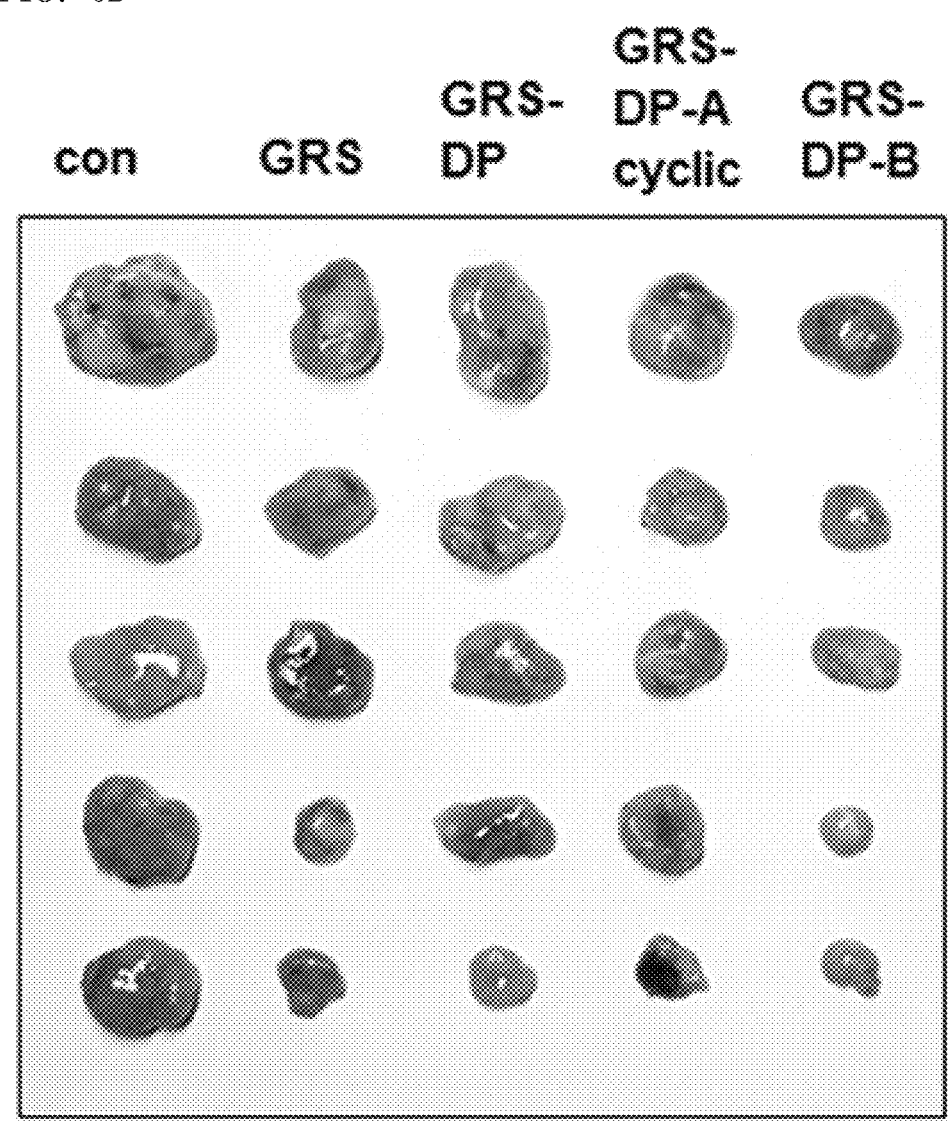

FIG. 6b is an image of tumors excised from experimental animals in each test group sacrificed on day 21 after xenotransplantation of tumor cells.

Figure 6C:
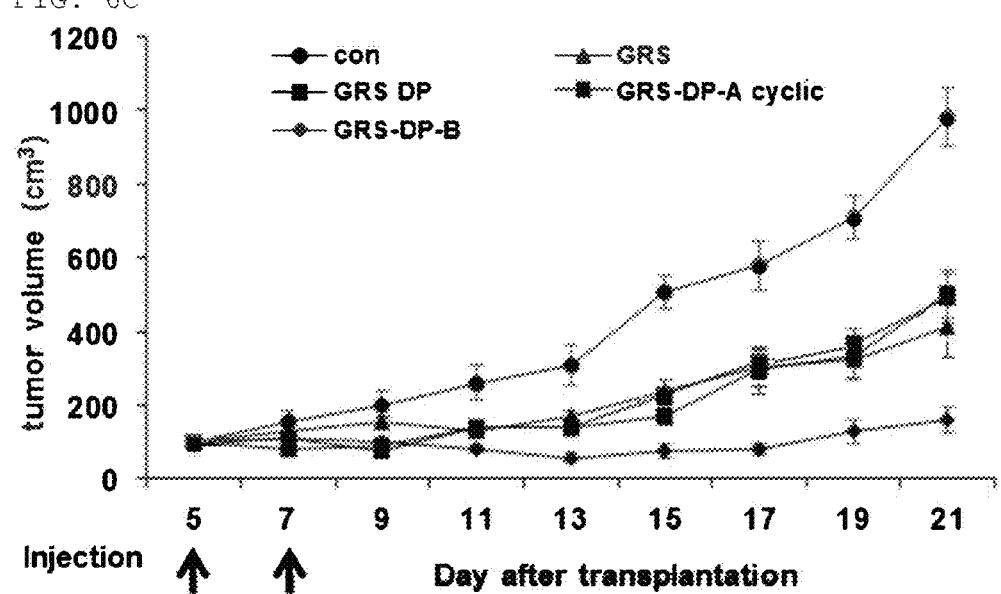

FIG. 6c shows monitoring results of tumor volumes in each test group with time.

Figure 6D:
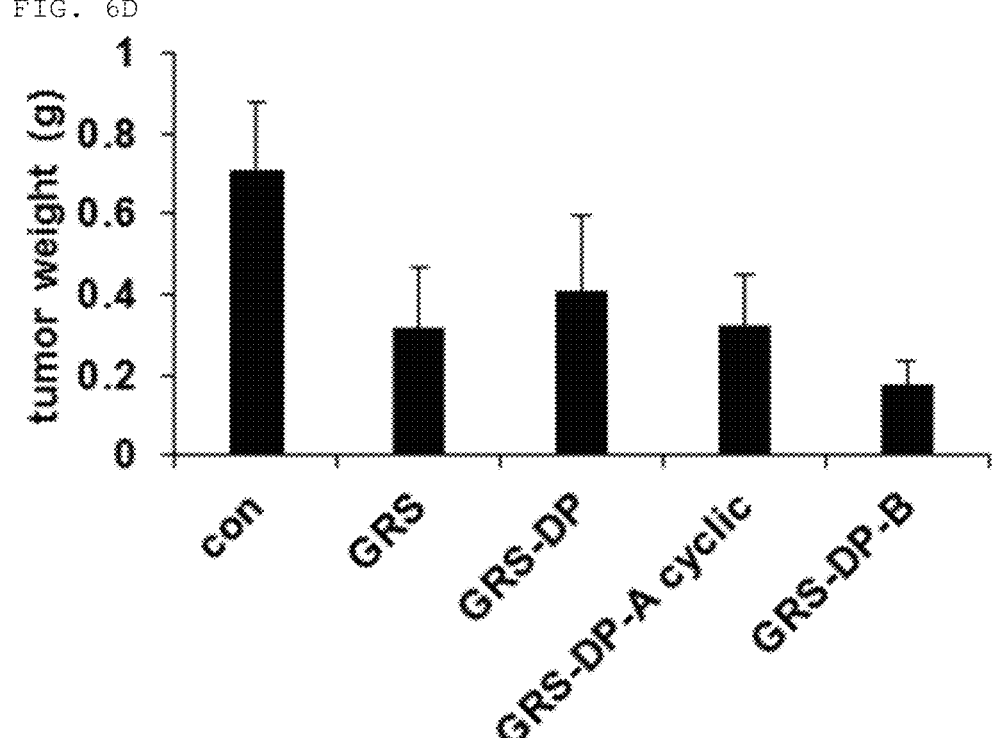

FIG. 6d shows weights of tumors finally obtained from experimental animals in each test group sacrificed on day 21 after xenotransplantation of tumor cells.

Figure 6E:
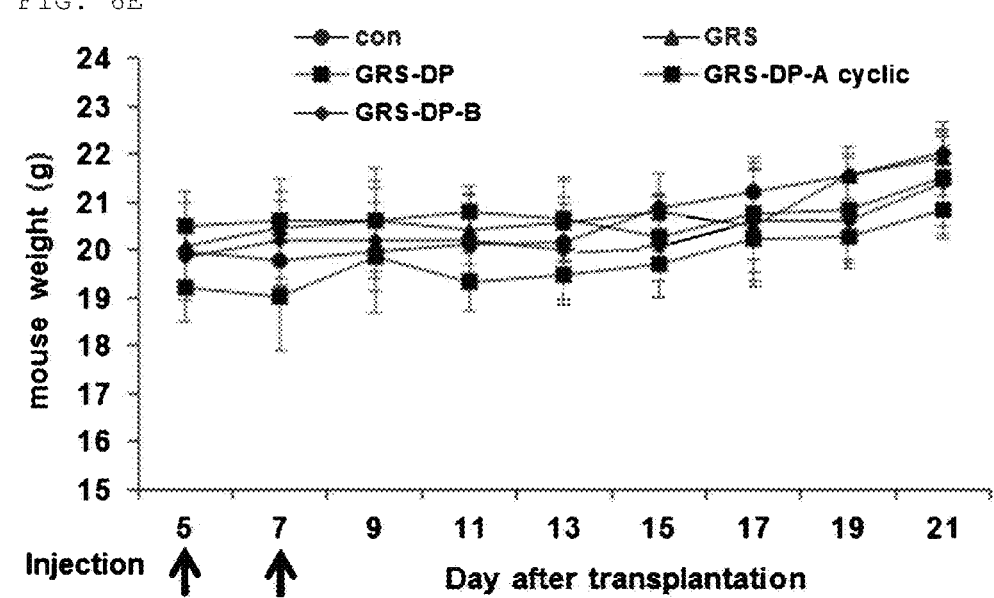

FIG. 6e shows monitoring results of weights of experimental animals in each test group with time.

Figure 7A:
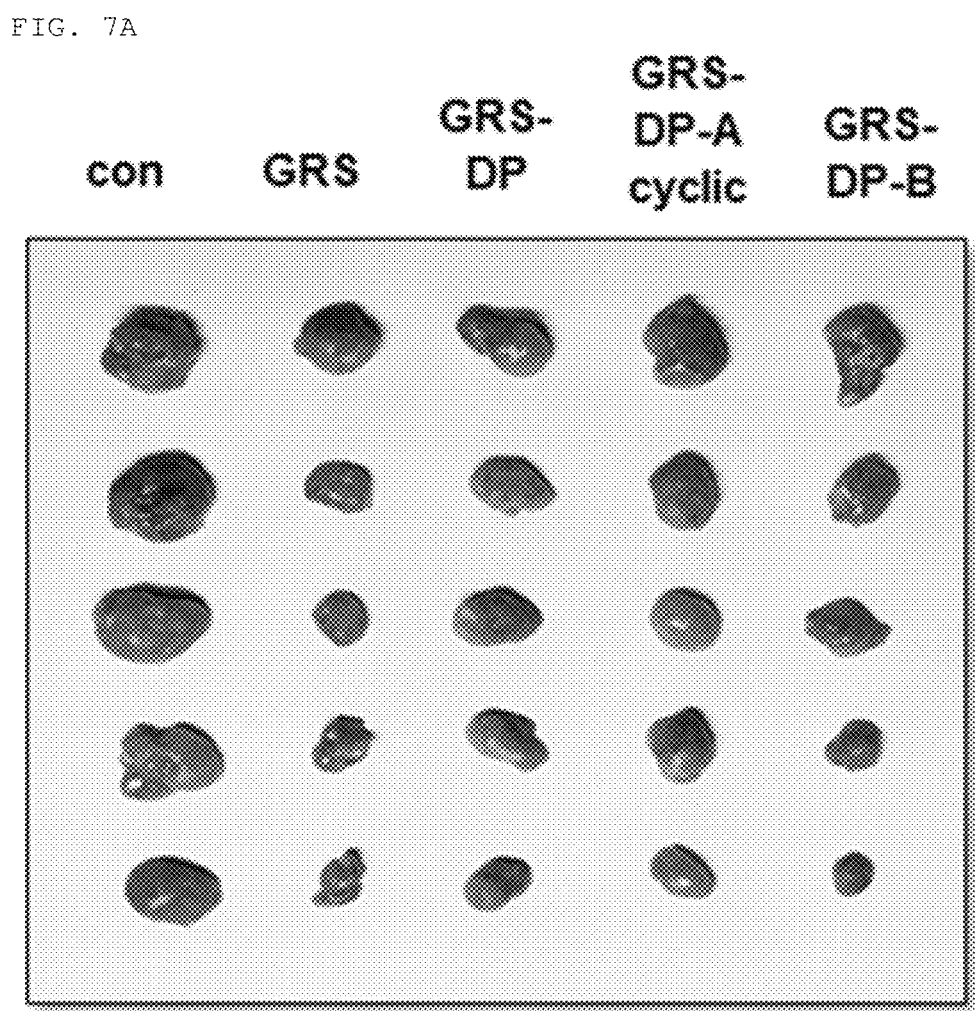

FIG. 7a is an image of tumors excised from experimental animals in each test group sacrificed on day 21 after xenotransplantation of tumor cells, showing results of evaluating the ability of GRS, GRS-DP, and representative fragments derived therefrom (GRS-DP-B, or GRS-DP-A cyclic) to induce tumor regression in vivo by intravenous injection. Briefly, SN12C (CDH6 positive) cells were subcutaneously injected into BALB/c nude mice and then grown for 5 days to an average tumor size of 100 mm$^3$. On day 5 and 7, PBS or test materials were each intravenously injected at a dose of 5 MPK (n=5 animals/group). Tumor volumes were calculated according to "maximum diameter×minimum diameter$^2$×0.52".

Figure 7B:
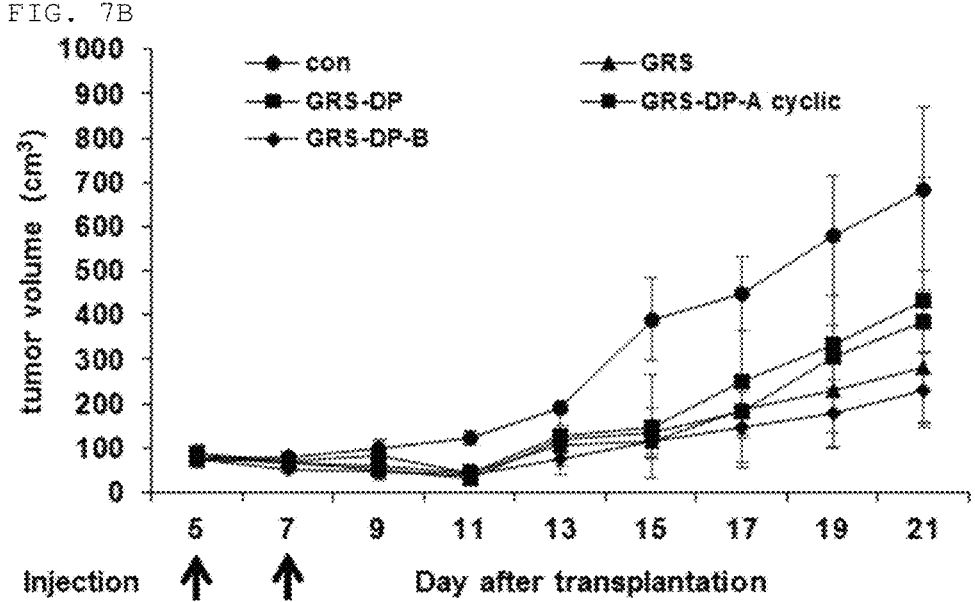

FIG. 7b shows monitoring results of tumor volumes in each test group with time.

Figure 7C:
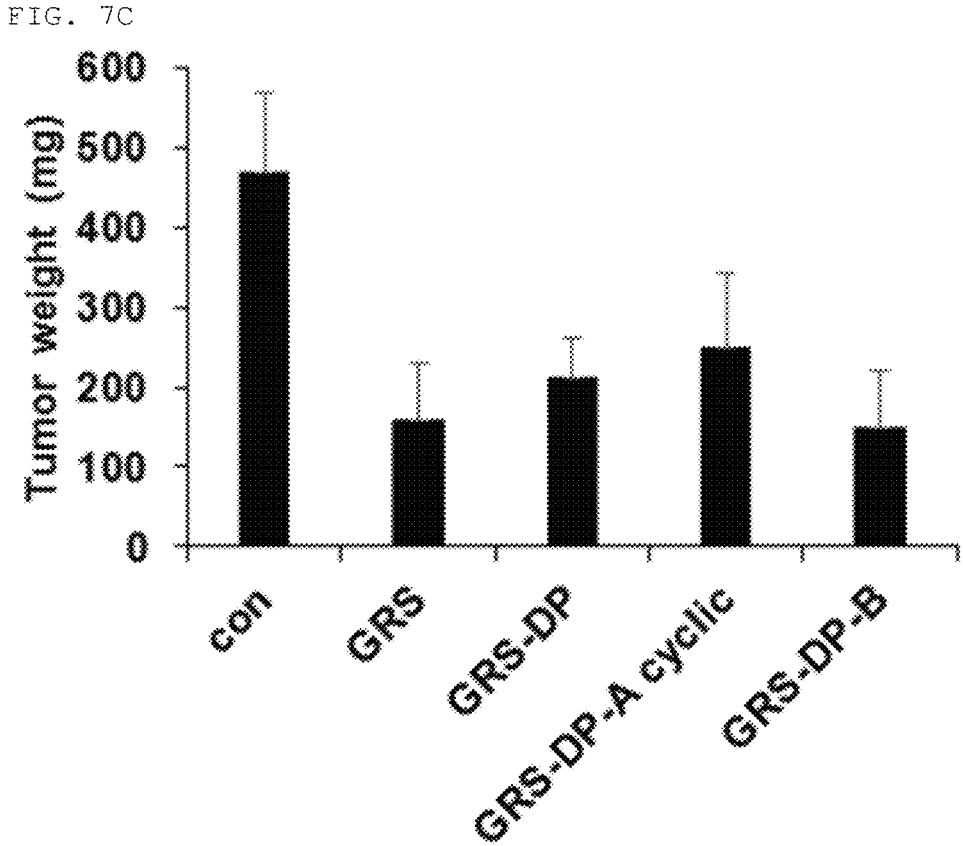

FIG. 7c shows weights of tumors finally obtained from experimental animals in each test group sacrificed on day 21 after xenotransplantation of tumor cells.

Figures 7D, 8A:
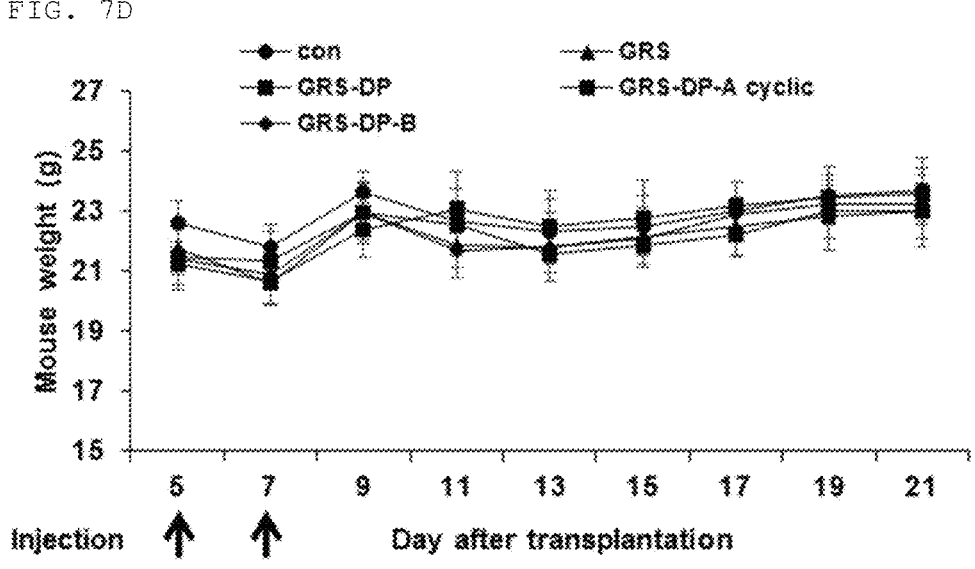

FIG. 7d shows monitoring results of weights of experimental animals in each test group with time.

FIG. 8a is an image of tumors excised from test groups, showing comparison of abilities of GRS, GRS-DP, and representative fragments derived therefrom (GRS-DP-B or GRS-DP-A cyclic) to specifically target cancer cells in terms of fluorescence labeling intensity. In the experiment, B16F10 cells were subcutaneously injected into C57BL/6 mice and then grown for 14 days. On day 14, PBS or fluorescence-labeled test materials were each intravenously injected at a dose of 1 MPK, and tumors were excised 24 hours after injection.

Figure 8B:
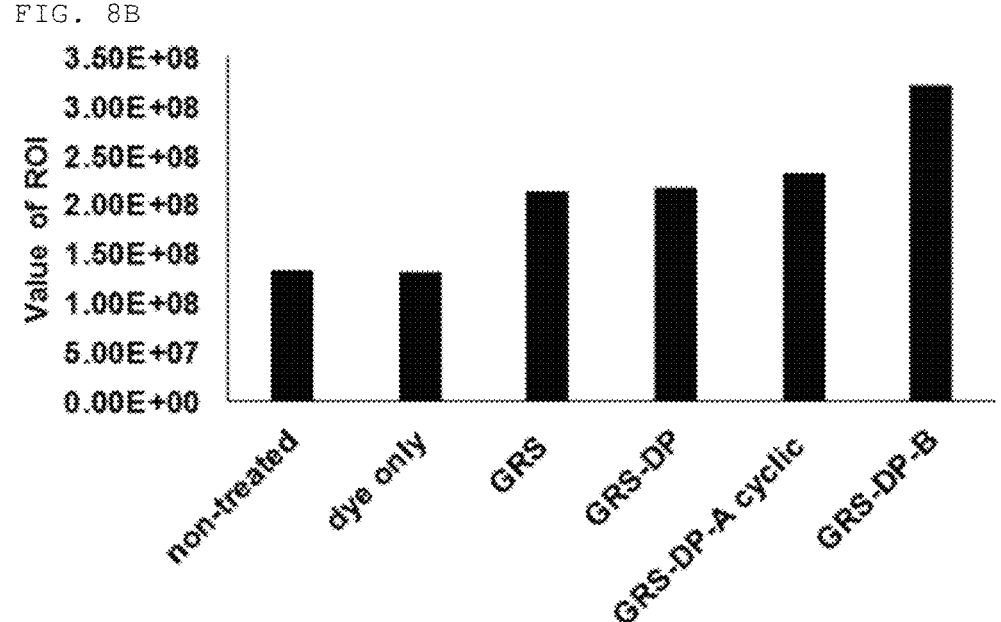

FIG. 8b shows relative fluorescence ROI values of tumors excised from each of the test groups of FIG. 8a.

MODE FOR CARRYING OUT THE INVENTION

Below, a detailed description will be given of the present invention.

While the approaches to be utilized in the invention have been described above, the techniques that are utilized are described in greater detail below. These examples are provided to illustrate the invention, and should not be construed as limiting.

Figure 1A:
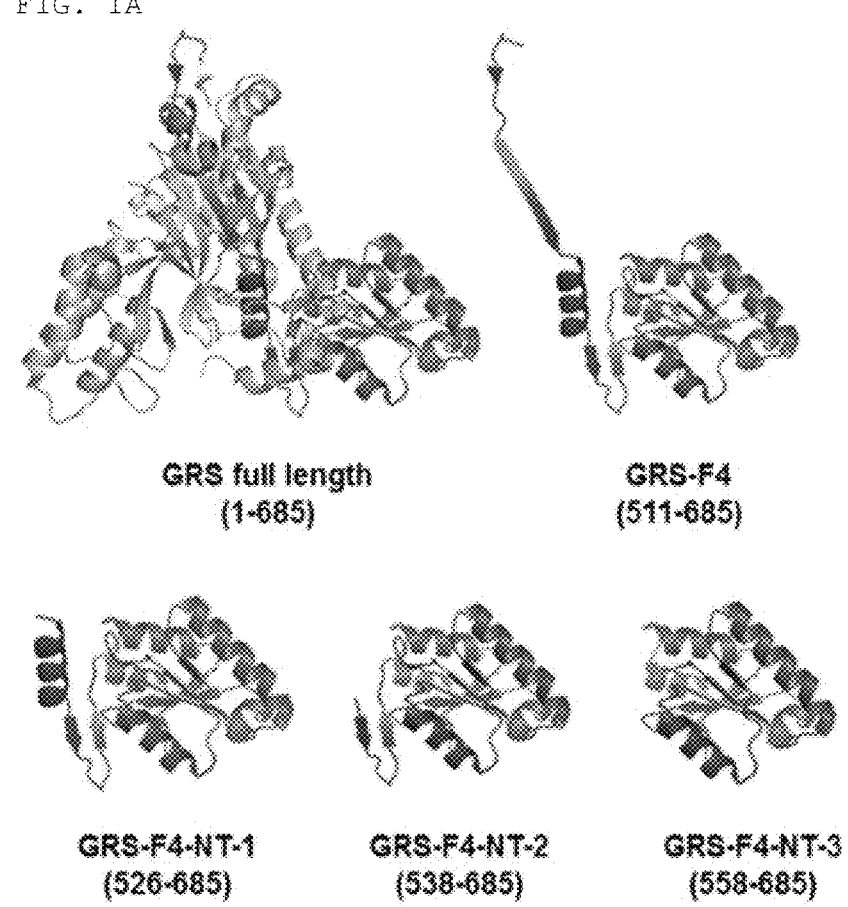
FIG. 1a shows 3D structures of full-length GRS protein and representative fragments of significant importance (GRS-F4, GRS-F4-NT-1, GRS-F4-NT2, and GRS-F4-NT3), which are members of peptide fragments constructed from C-terminal regions of GRS protein.
Figure 1B:
FIG. 1b shows 3D structures and features of representative fragments (GRS-DP, GRS-DP-A linear, GRS-DP-B, GRS-DP-C, and GRS-DP-A cyclic), which are members of peptide fragments constructed from C-terminal regions of GRS protein and variants thereof and are of significant importance in connection with an anticancer motif. From top to bottom: SEQ ID NO: 4, SEQ ID NO: 3, SEQ ID NO: 7, SEQ ID NO: 2, SEQ ID NO: 12.
Figure 1B:
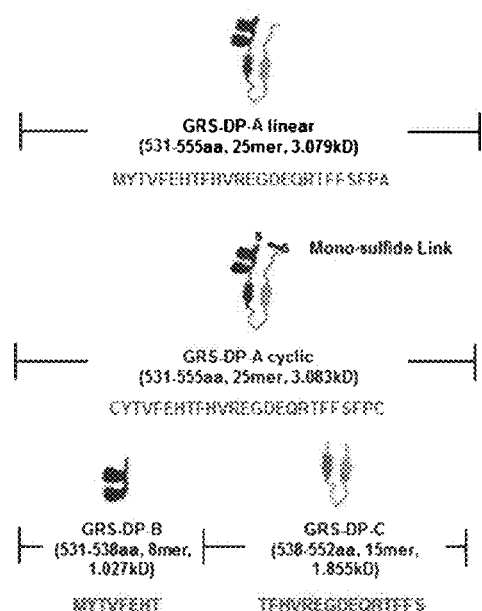

Example 1: Construction of GRS C Terminal-Derived Polypeptide and Assay for Anticancer Activity 1-1. Construction of GRS C-Terminal Fragment and Assay for Cancer Cell Apoptotic Activity From C-terminal regions of the full-length GRS protein (1-685, SEQ ID NO: 1), various polypeptide fragments were constructed. In Table 1, below, various polypeptide fragments (basically linear polypeptide) are listed. Among the various polypeptides in Table 1, some representative fragments of significant importance are depicted in FIGS. 1a and 1b in view of 3D structure. The polypeptide fragments were constructed by GL Biochem Shanghai Ltd, China (no 519 Ziyue road Minhang 200241 SHANGHAI SHANGHAI China) using solid phase synthesis.

The polypeptide fragments were assayed for cancer cell apoptotic activity. Concrete experiment procedures were as follows: H460, HCT116, MCF7, HeLa, SN12C or RENCA cells were each seeded at a density 5,000 cells/mL into 96-well plates (Corning, New York, USA) and incubated for 24 hours with 100 nM of each of the polypeptide fragments and the full-length GRS protein. Then, each sample was treated for 2 hours with 10 μl of CCK8 reagent (Dojindo Molecular Technologies Inc. Kumamoto, Japan) before absorbance was read at 570 nm on a microplate reader (TECAN, Mannedorf, Swiss).

The results of the cancer cell apoptotic assay exhibited that the polypeptide fragments GRS-F4, GRS-F4-NT-1, GRS-DP, GRS-DP-A (linear), GRS-DP-B, and those containing the regions thereof have cancer cell apoptotic activities similar to that of the full-length GRS protein, identifying the presence of an motif responsible for the anticancer activity in the 531-538 aa region of GRS-DP-B. In addition, this region showed that the anticancer activity motif is difficult to predict simply with structural analysis only.

1-2. Construction of GRS C-Terminal Fragment Variant and Assay for Cancer Cell Apoptotic Activity Variants were constructed by causing modifications (addition, deletion, or substitution) on the polypeptide fragments of Example 1-1. As such, peptides in cyclic forms as well as in linear forms were prepared according to modification methods.

First, linear polypeptide variants were synthesized by GL Biochem Shanghai Ltd, China (no 519 Ziyue road Minhang 200241 SHANGHAI SHANGHAI China) using a solid phase synthesis method. For cyclic variants, the linear peptides were allowed to undergo spontaneous cyclization by dissolving linear peptides at a concentration of $10^{-3}$-$10^{-4}$ M in water and adjusting the acidity to a pH of 8 with diluted ammonia. The cyclized structures were detected by comparing mass spectra of peptides before and after the reaction.

As a representative example, the variant sequence CYTVFEHTFHVREGDEQRTFFSFPC (25 a.a, SEQ ID

TABLE 1

| SEQ ID NO: | Form | Polypeptide name | Position (on SEQ ID NO: 1) | # of aa |
|---|---|---|---|---|
| 1 | full length | GRS | SEQ ID NO: 1 (1-685) | 685 |
| 14 | truncated | GRS-F4 | 511----------------------------------------685 | 175 |
| 6 | truncated | GRS-F4-NT-1 | 526------------------------------------685 | 160 |
| 37 | truncated | GRS-F4-NT-2 | 538---------------------------685 | 148 |
| 38 | truncated | GRS-F4-NT-3 | 558--------------------685 | 128 |
| 4 | truncated | GRS-DP | 531----------------------600 | 70 |
| 3 | truncated | GRS-DP-A | 531-------555 | 25 |
| 2 | truncated | GRS-DP-B | 531-538 | 8 |
| 12 | truncated | GRS-DP-C | 538--552 | 15 |
| 39 | truncated | GRS-EX-0 | 526--531 | 6 |
| 15 | truncated | GRS-EX-1 | 531--540 | 10 |
| 16 | truncated | GRS-EX-2 | 530--539 | 10 |
| 17 | truncated | GRS-EX-3 | 529--538 | 10 |
| 18 | truncated | GRS-EX-4 | 529----541 | 13 |
| 19 | truncated | GRS-EX-5 | 531----545 | 15 |
| 20 | truncated | GRS-EX-6 | 526---------545 | 20 |
| 21 | truncated | GRS-EX-7 | 524-------538 | 15 |
| 22 | truncated | GRS-EX-8 | 528-----540 | 13 |
| 23 | truncated | GRS-EX-9 | 531----550 | 20 |
| 24 | truncated | GRS-EX-10 | 519---------538 | 20 |
| 25 | truncated | GRS-EX-11 | 525-------541 | 19 |
| 26 | truncated | GRS-EX-12 | 511--------------540 | 30 |
| 40 | truncated | GRS-EX-13 | 511-----------535 | 25 |
| 27 | truncated | GRS-EX-14 | 527---------------561 | 35 |
| 41 | truncated | GRS-EX-15 | 540--------569 | 30 |
| 42 | truncated | GRS-EX-16 | 556------------------685 | 130 |
| 43 | truncated | GRS-EX-17 | 534----543 | 10 |
| 44 | truncated | GRS-EX-18 | 525-----534 | 10 |
| 28 | truncated | GRS-EX-19 | 516------------------------565 | 50 |
| 29 | truncated | GRS-EX-20 | 531-------------------580 | 50 |
| 30 | truncated | GRS-EX-21 | 525--------------------574 | 50 |
| 31 | truncated | GRS-EX-22 | 520---------------------569 | 50 |
| 32 | truncated | GRS-EX-23 | 528-------------------------603 | 76 |
| 45 | truncated | GRS-EX-24 | 577---------680 | 104 |
| 33 | truncated | GRS-EX-25 | 529------------------------628 | 100 |
| 46 | truncated | GRS-EX-26 | 533------------569 | 37 |
| 34 | truncated | GRS-EX-27 | 511------------------------------------630 | 120 |
| 35 | truncated | GRS-EX-28 | 530--------------------------679 | 150 |
| 36 | truncated | GRS-EX-29 | 515----------------------------------------684 | 170 |
| 5 | truncated | GRS-EX-30 | 531-------------------------------685 | 155 |

NO: 7) was prepared from the GRS-DP-A (linear) peptide and then cyclized. The resulting cyclic form was named "GRS-DP-A cyclic" herein. "GRS-DP-A cyclic" is a cyclic form in which a monosulfide linkage is formed between cysteine residues at the opposite termini.

1-3. Comparison of In Vitro Anticancer Activity Among the Polypeptides

Comparison was made of cancer cell apoptotic activity among the polypeptide constructs of Examples 1-1 and 1-2. Each polypeptide was used in an amount of 1 μg or 2 μg, and the assay was performed in the same manner as in Example 1-1.

Figure 2:
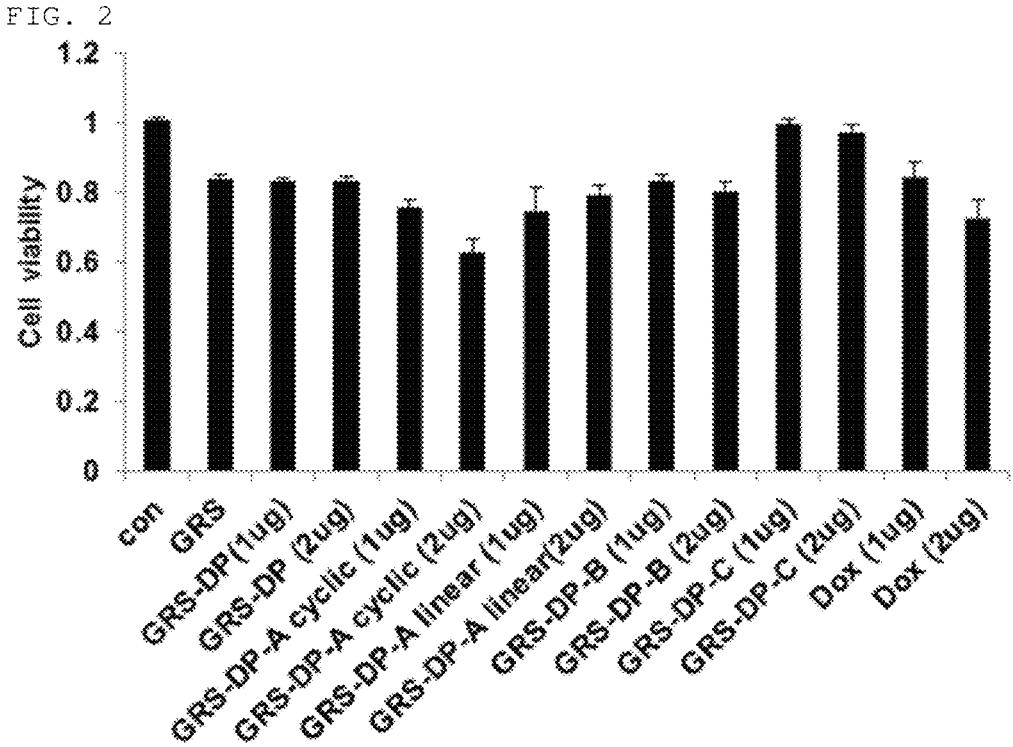
FIG. 2 shows relative cancer cell apoptotic activities of peptides after SN12C (CDH6 positive renal cancer cell) is treated with predetermined concentrations thereof.

FIG. 2 shows experimental results of some representative polypeptides (GRS-DP, GRS-DP-A linear, GRS-DP-A cyclic, GRS-DP-B, and GRS-DP-C) among the various polypeptides. As can be seen in FIG. 2, the cancer cell apoptotic effect was not detected in GRS-DP-C, but remarkably in GRS-DP, GRS-DP-A linear, GRS-DP-A cyclic, and GRS-DP-B. Characteristically, the variant GRS-DP-A cyclic was superior to its origin peptide GRS-DP-A in terms of anticancer cell apoptotic effect.

The representative polypeptides GRS-DP-A linear, GRS-DP-A cyclic, GRS-DP-B, and GRS-DP-C, which show characteristically significant anticancer activity as shown in FIG. 2, are depicted for features in FIG. 1b. Briefly, "GRS-DP-A linear" is a 25-mer polypeptide fragment covering the $1^{st}$ to $25^{th}$ amino acids from the N-terminus of GRS-DP (corresponding to 531-555 aa on GRS), defined by SEQ ID NO: 3, and having a molecular weight of 3.079 kDa. "GRS-DP-A cyclic", defined by SEQ ID NO: 7, was derived from GRS-DP-A linear by substituting each of the N-terminal methionine and the C-terminal alanine with cysteine. The cyclic form occurred as the cysteine residues at the opposite termini formed a monosulfide bond. It has a molecular weight of 3.083 kDa. "GRS-DP-B", defined by SEQ ID NO: 2, is an 8-mer fragment covering the $1^{st}$ to $8^{th}$ amino acids from the N-terminus of GRS-DP-A linear (corresponding to 531-538 aa on GRS) and isolated from a region of alpha helix structure. "GRS-DP-C", defined by SEQ ID NO: 12, is a 15-mer fragment covering the $8^{th}$ to $22^{nd}$ amino acids from the N-terminus of GRS-DP-A linear (corresponding to 538-552 aa on GRS) and isolated from a region of loop structure. "GRS-DP-B" and "GRS-DP-C" have molecular weights of 1.027 kDa and 1.855 kDa, respectively.

In full consideration of the result of Example 1-1 in which the anticancer activity motif is included in the region of 531-538 aa corresponding to GRS-DP-B (SEQ ID NO: 2) and the data of FIG. 2 in which GRS-DP-A cyclic showing anticancer activity is derived by substituting cysteine for the N-terminal methionine of GRS-DP-A linear (531-555 aa), the 532-538 aa region on full-length GRS protein (SEQ ID NO: 1) was finally identified as a motif critical for the anticancer activity.

1-4. Melting Temperature (Tm) of the Polypeptides

Some representative polypeptides that were identified to have excellent anticancer activity in Example 1-3 were measured for melting temperature (Tm), using a thermal shift assay, with the full-length GRS polypeptide serving as a control. Concrete experiment methods are as follows.

The experiment was performed using ProteoStat Thermal Shift Stability Assay (Enzo Life Sciences, Farmingdale, NY) according to the manufacturer's manual. In brief, the full-length GRS protein or the polypeptides of the present invention were each mixed at a concentration of 2 mg/mL with 10× PROTEOSTAT TS detection reagent. Each sample was heated in a linear gradient condition at 0.2° C./min from 25° C. to 99° C., and fluorescence was measured in triplicate using Thermal Cycler Dice™ Real Time system (Takara, Shiga, Japan) in the condition of 480 nm excitation and 615 nm emission.

Figure 3A:
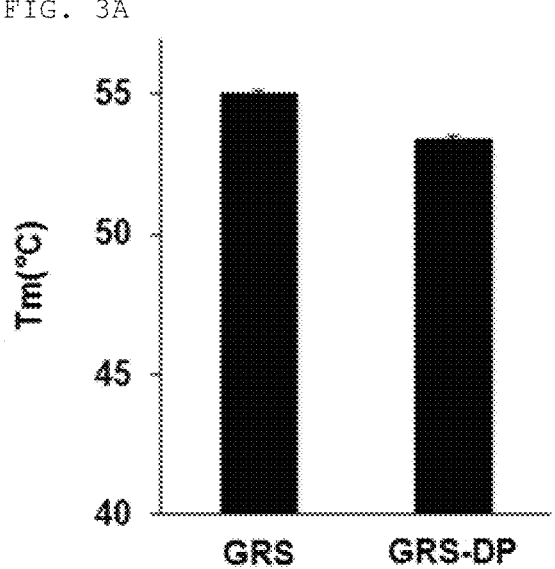
FIG. 3a shows Tm (melting temperature) of GRS-DP polypeptide of the present invention, as measured by thermal shift assay (full-length GRS protein serving as a control).
Figure 3B:
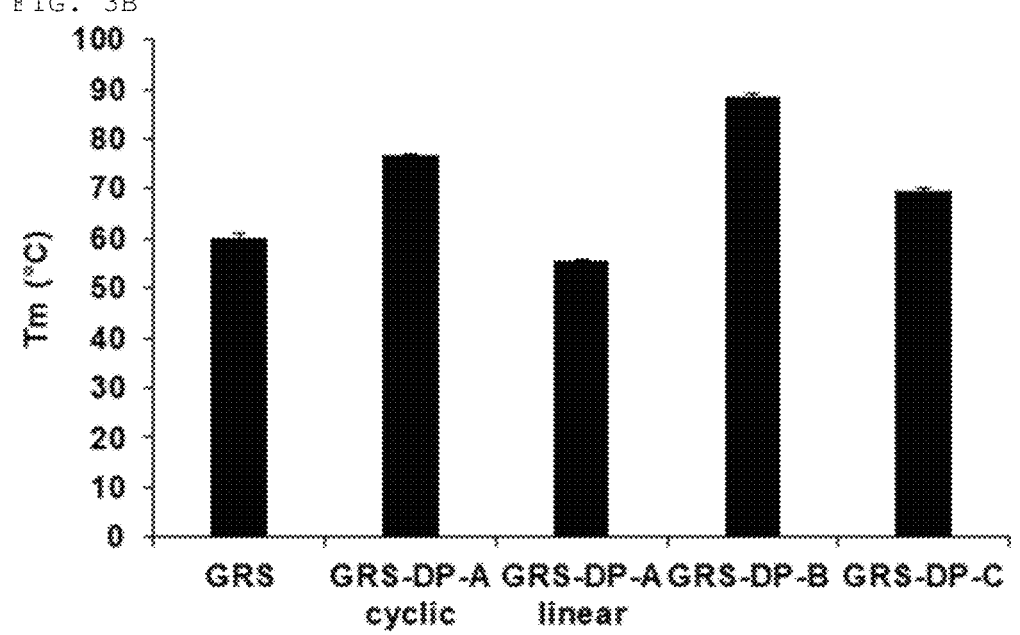
FIG. 3b shows Tm (melting temperatures) of GRS-DP-A cyclic, GRS-DP-A linear, GRS-DP-B, and GRS-DP-C, as measured by thermal shift assay (full-length GRS protein serving as a control).

As can be seen FIGS. 3a and 3b, GRS-DP, GRS-DP-A linear, GRS-DP-A cyclic, and GRS-DP-B showed Tm similar to or higher than that of the full-length GRS protein. In addition, GRS-DP-C serving as a control also showed Tm similar to that of GRS. Thus, GRS-DP-A linear, GRS-DP-A cyclic, GRS-DP-B, or respective polypeptides containing the same were identified to be as stable as or more stable than the full-length GRS protein.

1-5. CD (Circular Dichroism) Spectroscopy for the Polypeptides

Some representative polypeptides that were identified to have excellent anticancer activity in Example 1-3 were analyzed for structural characteristic by CD (circular dichroism) spectroscopy. CD spectroscopy was conducted as follows. Far UV CD spectra for the full-length GRS protein and the polypeptide samples were recorded as averages using 0.1 cm path length quartz SUPRASIL cell (Hemlla, Germany). J-815 Circular Dichroism machine (JASCO, Oklahoma City, USA) with a spectral resolution of 1.0 nm at a bandwidth of 1 nm and 2.0 s. Spectra for 600 μl of each of 1.0 mg/mL samples were averaged of 3 scans after blank subtraction.

Figure 4:
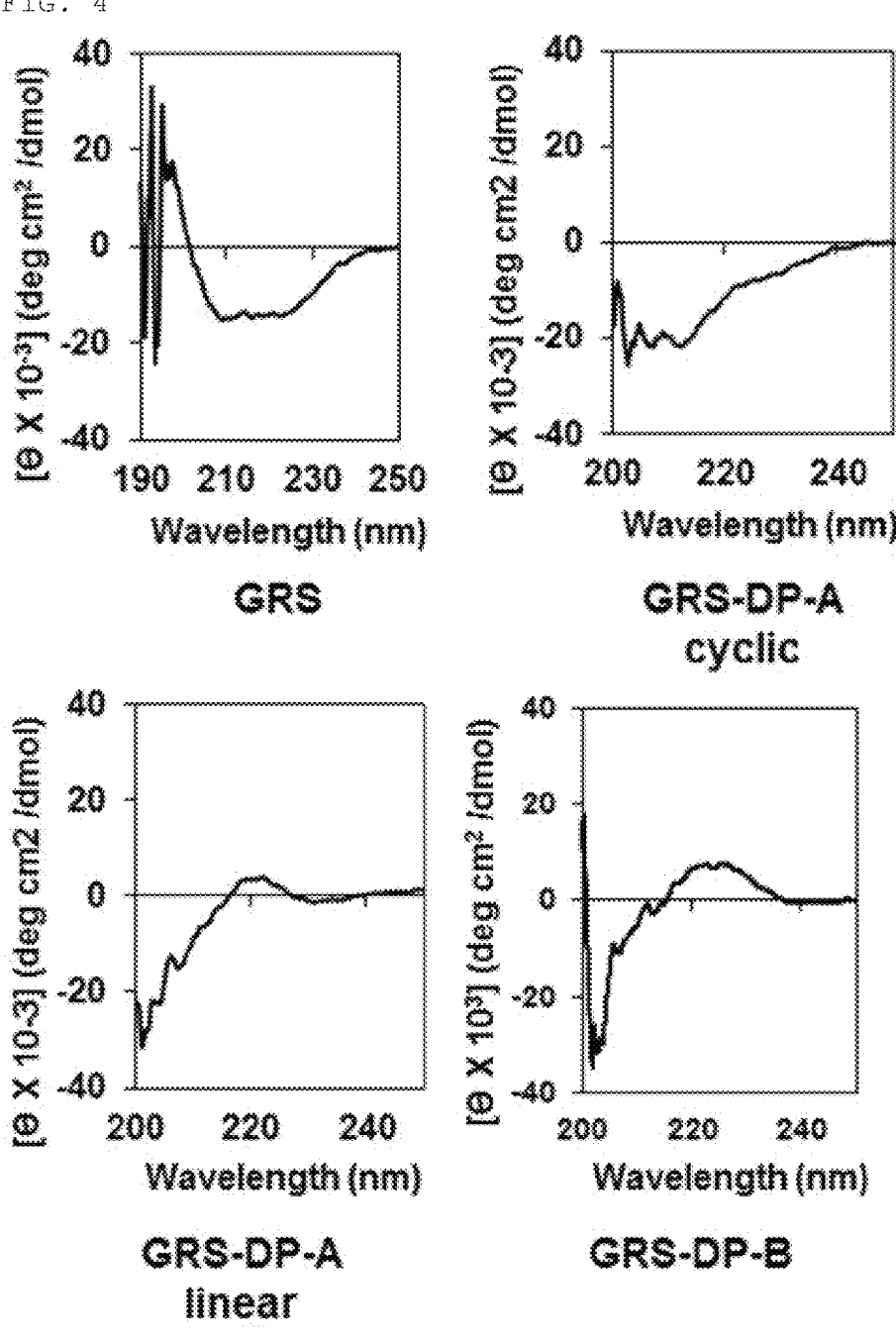
FIG. 4 shows CD (Circular dichroism) spectra of the fragments.

FIG. 4 shows CD analysis results for GRS-DP-A linear, GRS-DP-A cyclic, and GRS-DP-B, which are characteristically representative of the peptides and have excellent anticancer activity. Observation was made of an alpha-helix form structure in the full-length GRS protein, an N-extension helix form structure in both GRS-DP-A linear and GRS-DP-B, and the cyclic form structure intended in Example 1-1 in GRS-DP-A cyclic (see Ion mobility-mass spectrometry applied to cyclic peptide analysis: conformational preferences of gramicidin S and linear analogs in the gas phase Journal of the American Society for Mass Spectrometry Volume 15, Issue 6, June 2004, Pages 870-878/ Chemical Synthesis and Folding Pathways of Large Cyclic Polypeptides: Studies of the Cystine Knot Polypeptide Kalata B1Biochemistry, Vol. 38, No. 32, 1999 10606)

Example 2: In Vitro Anticancer Activity Mechanism 2-1. CDH6-Dependency

To examine whether the polypeptides of the present invention exhibits activity in a CDH6-dependent manner, CDH6 (Cadherin-6)– and pERK (Protein kinase R-like endoplasmic reticulum kinase)-positive cells (CDH6+/ pERK+) or negative cells were measured for cell viability in the presence of the polypeptides of the present invention. As a representative of the peptides, GRS-DP (100 nM) was used in the experiment. Briefly, H460 (CDH6+/pERK+), HeLa (CDH6+/pERK+), SN12C (CDH6+/pERK+), RENCA (CDH6⁻/pERK+), MCF7 (CDH6⁻/pERK⁻) cells were incubated for 1 hour with full-length GRS (100 nM) or GRS-DP (100 nM). After incubation, the cells were washed twice with PBS and lysed in a lysis buffer (150 mM NaCl, 2 mM EDTA, 1% Triton X-100, 1% sodium deoxycholate, 10 mM NaF, 1 mM orthovandadate, 10% glycerol, protease cocktail). Thirty micrograms of each protein were run on SDS/ PAGE, followed by western blotting with an ERK antibody purchased from Cell Signaling Technology (Danvers, MA, USA) and an anti-cadherin-6 (K-cadherin) antibody purchased from Abcam (Cambridge, UK).

Figures 5A, 5B:
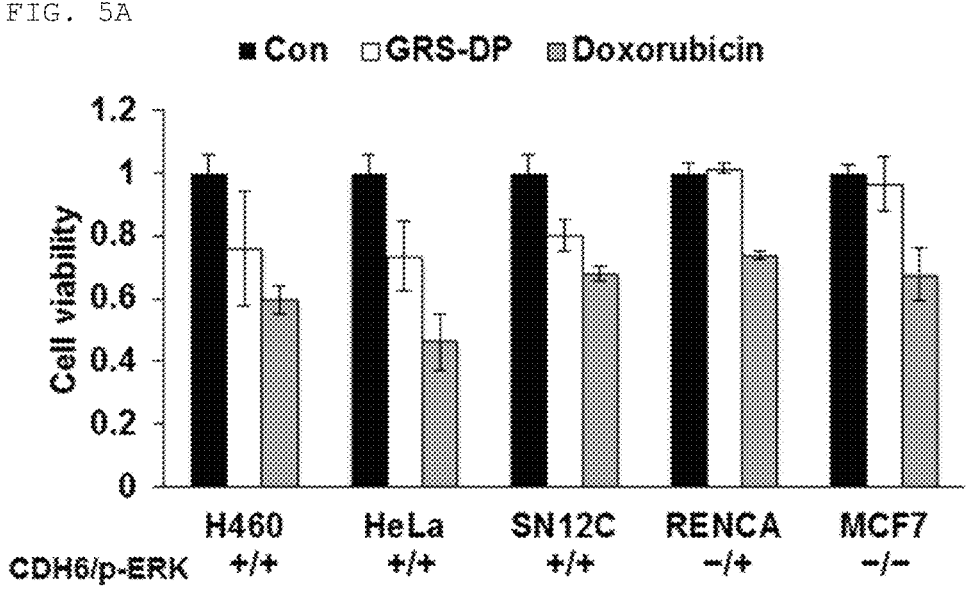
FIG. 5a shows cell viability of CDH6– and pERK– positive cells (CDH6$^+$/pERK$^+$) or negative cells after treatment with GRS-DP (200 nM) to determine CDH-dependent action (doxorubicin 100 nM serving as a positive control).
FIG. 5b shows extents of dephosphorylation of pERK after the treatment of SN12C (CDH6 positive) cells with 100 nM or 200 nM of GRS-DP (GRS 100 nM serving as a positive control).

As shown in FIG. 5a, GRS-DP polypeptide reduced the cell viability of CDH6-positive cells only. Therefore, the polypeptides of the present invention were found to act in a CDH6-dependent manner.

2-2. Anticancer Activity Mechanism of GRS-DP

To examine whether the polypeptides of the present invention dephosphorylates pERK by binding to CDH6 or not, SN12C (CDH6 positive) cells or RENCA (CDH6 negative) cells were treated with the polypeptides of the present invention (typically, 100 nM or 200 nM of GRS-DP) and dephosphorylation of pERK was analyzed. In this regard, full-length GRS 100 nM was used as a positive control. In brief, the cells were washed for 1 hour with full-length GRS or GRS-DP, washed twice with chilled PBS, and lysed in a lysis buffer (150 mM NaCl, 2 mM EDTA, 1% Triton X-100, 1% sodium deoxycholate, 10 mM NaF, 1 mM orthovandadate, 10% glycerol, protease cocktail). Thirty micrograms of each protein were run on SDS/PAGE, followed by western blotting with an ERK antibody purchased from Cell Signaling Technology (Danvers, MA, USA) and an anti-cadherin-6 (K-cadherin) antibody purchased from Abcam (Cambridge, UK).

Figure 5C:
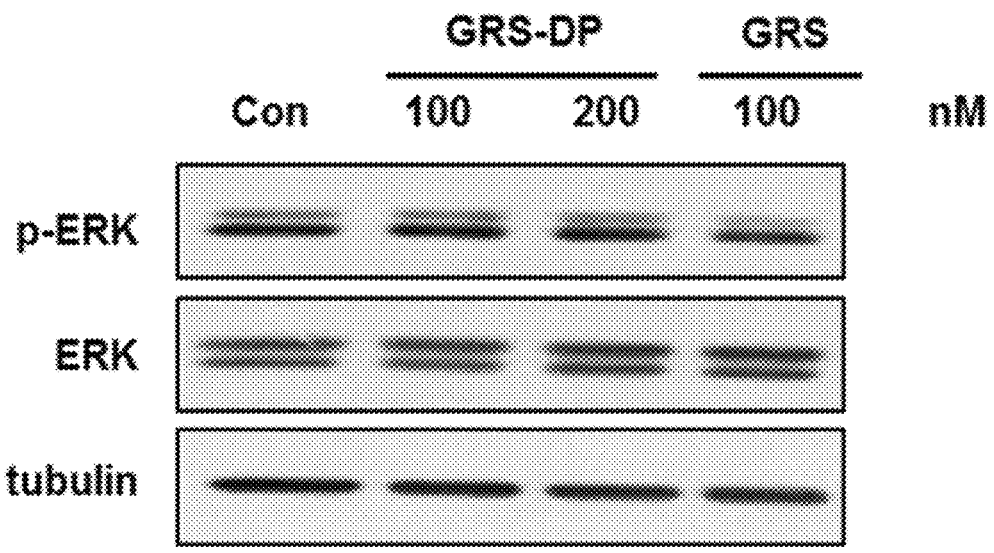
FIG. 5c shows extents of dephosphorylation of pERK after the treatment of RENCA (CDH6 negative) cells with 100 nM or 200 nM of GRS-DP (GRS 100 nM serving as a positive control).

As shown in FIGS. 5b and 5c, GRS-DP polypeptide was found to mediate cancer cell apoptosis by inducing the CDH6-dependent dephosphorylation of pERK.

2-3. Comparison of Interaction with CDH6

Comparison was made of the affinity of the peptides of the present invention for CDH6. The binding of GRS and GRS-derived peptides to cadherin6 (CDH6)-fc fusion protein was analyzed by surface plasmon resonance (SPR) using SR7500DC, Reichert Analytical Instrument (Depew NY). CDH6 was immobilized on a [CMDH chip]carboxymethyl dextran sensor chip via a free carboxyl group on the surface thereof, followed by injecting 0.1M 1-ethyl-3-(3-dimethylaminopropyl) carbodiimide hydrochloride and 0.05M N-hydroxysuccinimide at a flow speed of 5 μL/min to give an activated succinimide ester-modified surface. Various concentrations of GRS and GRS-derived peptides were injected at a flow speed of 30 μL/min into phosphate-based saline, after which a mobile-phase buffer was injected at the same flow speed to determine a dissociation rate. Data was analyzed using Software Scrubber 2.0 (Biological Software, Australia).

Figure 5D:
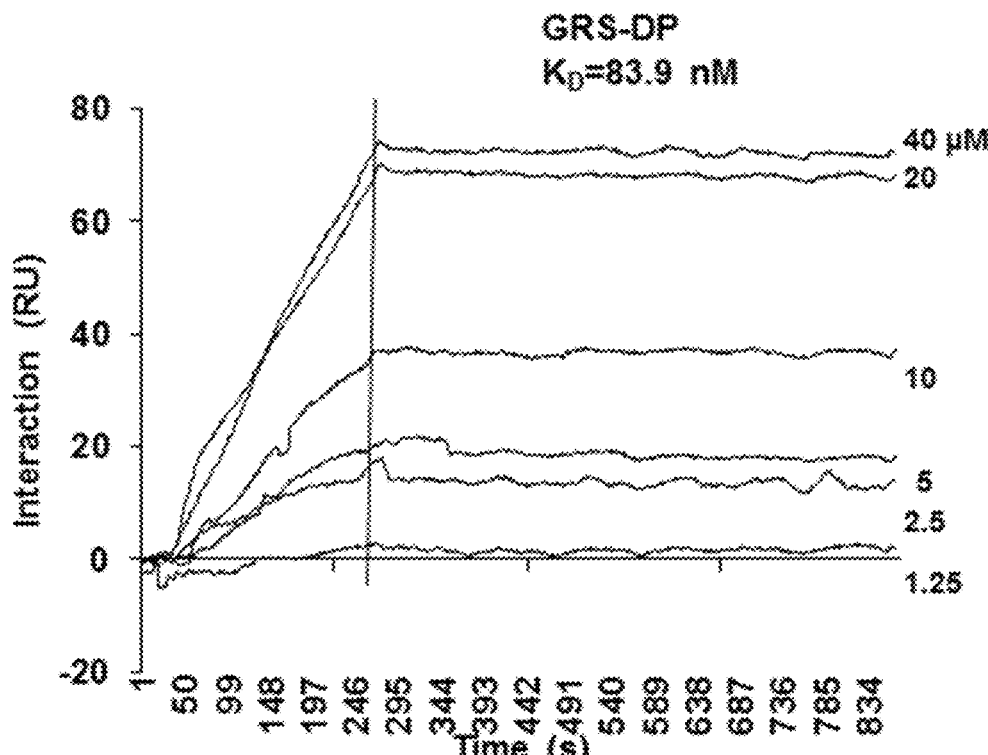
FIG. 5d shows affinity of GRS-DP polypeptide of the present invention for CDH6 as measured by SPR (Surface Plasmon Resonance).
Figure 5E:
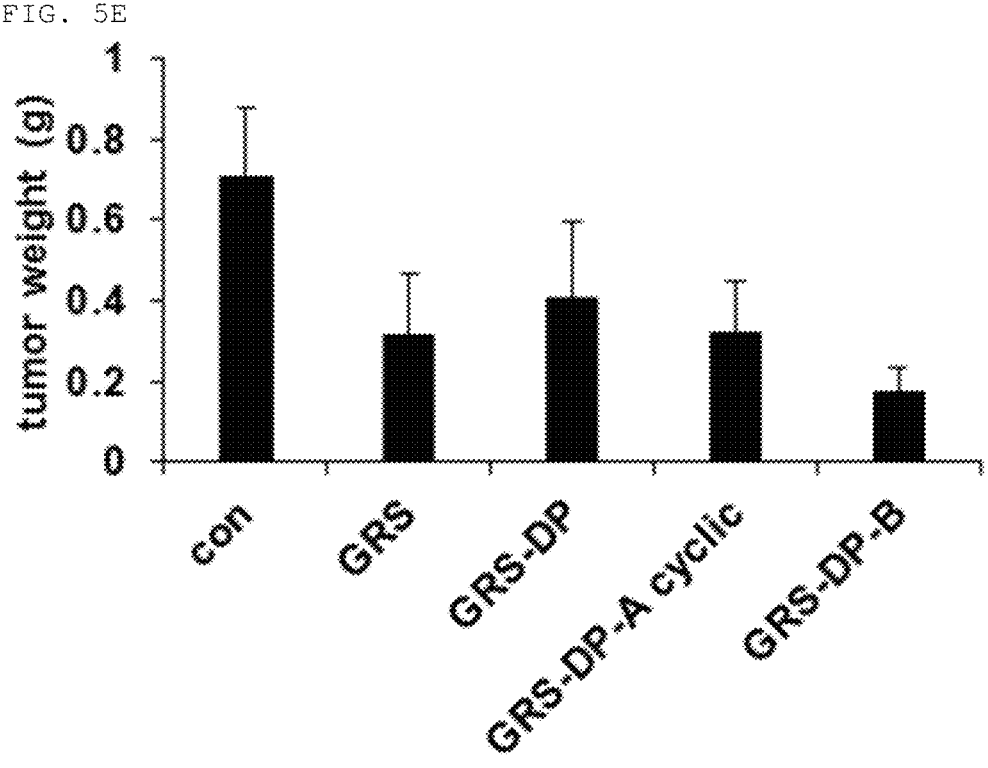
FIG. 5e shows affinity of GRS-DP-A linear polypeptide of the present invention for CDH6 as measured by SPR (Surface Plasmon Resonance).
Figure 5F:
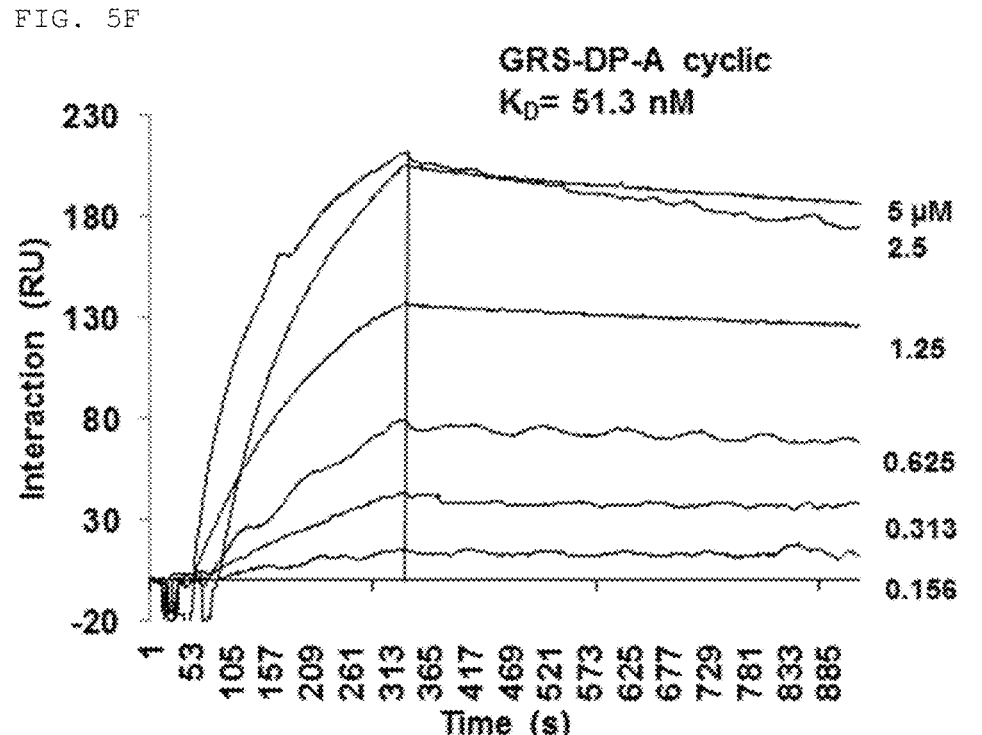
FIG. 5f shows affinity of GRS-DP-A cyclic polypeptide of the present invention for CDH6 as measured by SPR (Surface Plasmon Resonance).

FIGS. 5d to 5f show representative examples of results of affinity assays for the peptides of the present invention. GRS-DP peptide was observed to have $K_D$=83.9 nM while its shorter fragment GRS-DP-A linear showed better affinity with $K_D$=61.2 nM. Specifically, GRS-DP-A cyclic, which is derived from GRS-DP-A linear, was measured to have $K_D$=51.3 nM, exhibiting far better affinity for CDH6. Through the experiments, it was found that the polypeptide fragments containing the anticancer motif have higher affinity for CDH6 as their length is shorter. Particularly, when structured to have a cyclic form, they exhibited unpredictable effects.

Example 3: Comparison of In Vivo Anticancer Activity and Cancer Cell Targeting Ability Between the Peptides 3-1. Comparison of In Vivo Anticancer Activity Between the Polypeptides_IT Injection Some representative peptides (GRS-DP, GRS-DP-B, and GRS-DP-A cyclic) that were identified to have excellent anticancer activity in Example 1-3 were used as test substances while full-length GRS protein served as a control.

Experimental procedures of an assay for in vivo anticancer activity are schematically represented in FIG. 6a. Briefly, $1 \times 10^7$ SN12C (CDH6 positive) cells were subcutaneously injected to the right flank of female BALB/c 8 weeks old (Dooyeol Biotech Co. Ltd, Seocho-gu, Seoul) and then grown for 5 days to an average tumor size of 100 mm³. On day 5 and 7, PBS (control) or test materials (including a control) were each injected at a dose of 20 μg into tumors (n=5 animals/group). After monitoring the tumors for 21 days, the mice were sacrificed on day 21 and the tumors were excised. Tumor volumes were calculated according to "maximum diameter×minimum diameter²×0.52". Test results are shown in FIGS. 6b to 6e.

As shown in FIGS. 6b to 6d, sizes (volumes) and weights of tumors were most remarkably reduced in the shortest fragment GRS-DP-B (8-mer). Particularly, such tumor regression effects were far higher, compared to those from full-length GRS protein and GRS-DP. Short fragments containing the anticancer motif (532-538 aa.) first revealed in the present invention, isolated from the full-length GRS protein, were found to have butter anticancer activity, compared to the intact protein. GRS-DP-A cyclic was also observed to exhibit a significant anticancer effect in vivo (see FIGS. 6b to 6d).

As shown in FIG. 6e, mice in each test group did not undergo a significant change in weight, compared to the control. Taken together, the data obtained in this test indicate that the polypeptide fragments constructed in the present invention are free of toxicity in vivo.

3-2. In Vivo Anticancer Activity of Polypeptide_IV Injection

As opposed to direct intratumoral injection in Example 3-1, efficacy was evaluated by intravenous injection in this Example. Some representative polypeptides (GRS-DP, GRS-DP-B, and GRS-DP-A cyclic) that had been identified to have excellent anticancer activity in Example 1-3 were used as test substances while full-length GRS protein served as a control.

Experimental procedures of an assay for in vivo anticancer activity are schematically represented in FIG. 6a. Briefly, $1 \times 10^7$ SN12C (CDH6 positive) cells were subcutaneously injected to the right flank of female BALB/c 8 weeks old (Dooyeol Biotech Co. Ltd, Seocho-gu, Seoul) and then grown for 5 days to an average tumor size of 100 mm³. On day 5 and 7, PBS (control) or test materials (including a control) were each intravenously injected at a dose of 5 MPK (n=5 animals/group). After monitoring the tumors for 21 days, the mice were sacrificed on day 21 and the tumors were excised. Tumor volumes were calculated according to "maximum diameter×minimum diameter²×0.52". Test results are shown in FIGS. 7a to 7d.

As shown, sizes (volumes) and weights of tumors were most remarkably reduced in the GRS-DP-B group. Particularly, such tumor regression effects were far higher, compared to those from full-length GRS protein and GRS-DP (FIGS. 7a to 7c). In light of systemic administration such as intravenous injection, it is important to target a certain drug specifically toward a tumor site in order to achieve an advantageous anticancer effect without side effects when administered in a systemic manner. GRS-DP-A cyclic was also observed to have a significant level of anticancer effect in vivo (see FIGS. 7a to 7c).

As shown in FIG. 7d, mice in each test group did not undergo a significant change in weight, compared to the control. Taken together, the data obtained in this test indicate that the polypeptide fragments constructed in the present invention are free of toxicity in vivo.

3-3. Ability of GRS-DP-Derived Small Fragments to Target Cancer Cells_IV Injection Even when administered in a systemic manner, GRS-DP-B was observed to exhibit the most remarkable anticancer effect in Example 3-2. Thus, the ability of GRS-DP-B to target tumors in practice was evaluated when it was administered in a systemic manner. For this, GRS-DP-B, GRS-DP-A cyclic, GRS-DP, and full-length GRS protein were assayed for tumor targeting ability in vivo. Briefly, B16F10 cells ($5\times10^6$ cells) were subcutaneously injected into the right flank of each of C57BL/6 mice 8 weeks old. On day 14, full-length GRS and the polypeptides of the present invention, each labeled with Alexa fluor 488, were intravenously injected at a dose of 1 mg/kg mouse weight, and the tumors were excised after 24 hours. Fluorescent signals of tumors were measured using IVIS Lumina Series III (PerkinElmer, Massachusetts, USA) to analyze regions of interest (ROI)

As can be seen in FIGS. 8a and 8b, remarkably high tumor-specific target ability was detected from GRS-DP-B, compared to full-length GRS protein and GRS-DP polypeptide. Therefore, GRS-DP-B per se can be used as an anticancer drug. In addition, the ability of the fragment to specifically targeting tumor sites allows the detection and imaging of tumors concurrently with the treatment of the tumors. Furthermore, when conjugated with an anticancer drug, the fragment exhibited a synergistic effect on anticancer treatment. Consequently, the polypeptides of the present invention have very advantageous values.

INDUSTRIAL APPLICABILITY

As described hitherto, the present invention relates to a fragmented GRS polypeptide, a variant thereof, and a use thereof and, more particularly, to an isolated polypeptide consisting of 8 to 170 consecutive amino acids, which contain the amino acids from positions 531 to 538 on the amino acid sequence defined by SEQ ID NO: 1; or a variant having a sequence homology of 80% or more to the isolated polypeptide, a fusion protein comprising the polypeptide, and a complex comprising the polypeptide, a polynucleotide coding for the polypeptide, and uses thereof in preventing and treating a neoplastic disease, in detecting cancer cells, in imaging cancer cells, and in delivering a drug to cancer cells.

The polypeptides (polypeptides isolated from GRS, and variants thereof) disclosed herein contain the GRS cell apoptotic motif first found in the present invention and are provided as truncated forms having certain lengths. The polypeptides exhibit far higher activity and targeting ability than the full-length protein and the domain, finding high industrial availability in the medicinal industry.

---

The invention claimed is:

1. A polypeptide comprising SEQ ID NO: 7 and 90% or more sequence identity to SEQ ID NO: 1, wherein the polypeptide is 25-160 amino acid residues in length and induces apoptosis in cancer cells.

2. The polypeptide of claim 1, wherein the polypeptide consists of the amino acid sequence defined by SEQ ID NO: 7.

3. The polypeptide of claim 1, wherein the polypeptide is 25 to 100 amino acid residues in length.

4. The polypeptide of claim 1, wherein the polypeptide is 25 to 50 amino acid residues in length.

5. The polypeptide of claim 1, wherein the polypeptide is in a linear or cyclic form.

6. A dimeric or multimeric complex, comprising at least one polypeptide of claim 1.

7. A polynucleotide encoding the polypeptide of claim 1.

8. An expression vector comprising the polynucleotide of claim 7.

9. A host cell comprising the expression vector of claim 8.

10. A composition, comprising a physiologically acceptable carrier and at least one selected from the group consisting of:
(i) the polypeptide of claim 1,
(ii) a dimeric or multimeric complex comprising at least one polypeptide of (i),
(iii) a polynucleotide encoding (i) and/or (ii),
(iv) an expression vector comprising (iii), and
(v) a host cell comprising (iv).

11. A composition comprising the polypeptide of claim 1 and a pharmaceutically acceptable excipient.

12. A screening method for identifying an anticancer agent, the method comprising the steps of:
a. forming a reaction mixture containing the polypeptide of claim 1 and a test compound; and
b. determining an increase in an anti-cancer activity by the polypeptide in the presence of the test compound, wherein an increase in the anti-cancer activity in the presence of the test compound is determined compared to the anti-cancer activity in the absence of the test compound, thereby identifying an active test compound.

13. A method for detecting cancer cells, the method comprising the steps of:
a. mixing the polypeptide of claim 1 with a biological sample;
b. removing the polypeptides that remain unbound or are non-specifically bound; and
c. determining whether and where the polypeptides are bound.

14. A method for treatment of a Cadherin-6 (CDH6)-positive neoplastic disease, the method comprising a step of administering to a subject in need thereof an effective amount of the polypeptide of claim 1 as an active ingredient.

15. The method of claim 14, wherein the neoplastic disease is selected from the group consisting of colon cancer, cardiac tumors, pancreatic cancer, melanoma, retinoblastoma, glioblastoma, lung cancer, intestinal cancer, testicular cancer, stomach cancer, neuroblastoma, osteosarcoma, chondrosarcoma, adenoma, breast cancer, prostate cancer, Kaposi's sarcoma, cervical cancer, multiple myeloma, renal cell carcinoma, solid tumor, and angiogenesis-related diseases.

16. A method for detecting or imaging cancer cells, the method comprising a step of administering to a subject in need thereof an effect amount of the polypeptide of claim 1 as an active ingredient.

17. A fusion protein, comprising a GRS peptide fragment and a heterologous fusion partner, wherein the GRS peptide fragment is 8-160 amino acid residues in length and comprises a sequence selected from the group consisting of SEQ ID NO: 2 and SEQ ID NO: 7.

18. The fusion protein of claim 17, wherein the heterologous fusion partner is an antibody or fragment thereof.

19. The fusion protein of claim 18, wherein the fragment is selected from the group consisting of an Fc, diabody, Fab, Fab', F(ab)2, F(ab')2, Fv, and scFv.

20. A composition comprising the fusion protein of claim 17, wherein the heterologous fusion partner comprises an anticancer agent.

21. A method for the treatment of cancer, the method comprising a step of administering to a subject in need thereof an effective amount of the composition of claim 20.

22. The fusion protein of claim 17, wherein the GRS peptide fragment is encoded by a nucleic acid sequence selected from the group consisting of SEQ ID NOs: 8 to 11.

23. A method for detecting or imaging cancer cells, the method comprising a step of administering to a subject in need thereof an effective amount of the fusion protein of claim 17, wherein the heterologous fusion partner comprises a label selected from the group consisting of a chromogenic enzyme, a radionuclide, a chromophore, a luminescent substance, a fluorescer, a super paramagnetic particle, and an ultrasuper paramagnetic particle.

24. A method for cancer cell-specific drug delivery, the method comprising a step of administering to a subject in need thereof an effective amount of the fusion protein of claim 17, wherein the heterologous fusion partner comprises a drug as an active ingredient.

25. The method of claim 24, wherein the drug is selected from the group consisting of paclitaxel, doxorubicin, vincristine, daunorubicin, vinblastine, actinomycin-D, docetaxel, etoposide, teniposide, bisantrene, homoharringtonine, cisplatin, 5-fluorouracil, adriamycin, methotrexate, busulfan, chlorambucil, cyclophosphamide, melphalan, nitrogen mustard, nitrosourea, streptokinase, urokinase, alteplase, an angiotensin II inhibitor, an aldosterone receptor inhibitor, erythropoietin, an NMDA (N-methyl-d-aspartate) receptor inhibitor, lovastatin, rapamycin, celebrex, ticlopin, marimastat, and trocade.

* * * * *